US012616695B2

(12) United States Patent
Brysch et al.

(10) Patent No.: US 12,616,695 B2
(45) Date of Patent: May 5, 2026

(54) USE OF 5-AMINO-2,3-DIHYDRO-1,4-PHTHALAZINE-DIONE IN THE TREATMENT OF RARE CHRONIC INFLAMMATORY PULMONARY DISEASES

(71) Applicant: Metriopharm AG, Zurich (CH)

(72) Inventors: Wolfgang Brysch, Berlin (DE); Astrid Kaiser, Berlin (DE); Petra Schulz, Berlin (DE); Sara Schumann, Seddiner See (DE); Jörg von Wegerer, Berlin (DE)

(73) Assignee: Metriopharm AG, Zurich (CH)

( * ) Notice: Subject to any disclaimer, the term of this patent is extended or adjusted under 35 U.S.C. 154(b) by 637 days.

(21) Appl. No.: 17/791,460

(22) PCT Filed: Jan. 29, 2021

(86) PCT No.: PCT/EP2021/000012
§ 371 (c)(1),
(2) Date: Jul. 7, 2022

(87) PCT Pub. No.: WO2021/151620
PCT Pub. Date: Aug. 5, 2021

(65) Prior Publication Data
US 2023/0053455 A1 Feb. 23, 2023

(30) Foreign Application Priority Data
Jan. 31, 2020 (EP) ..................................... 20000050

(51) Int. Cl.
*A61K 31/502* (2006.01)
*A61P 11/00* (2006.01)
(52) U.S. Cl.
CPC ............ *A61K 31/502* (2013.01); *A61P 11/00* (2018.01); *A61K 2800/40* (2013.01)
(58) Field of Classification Search
CPC ............................... A61K 31/502; A61P 11/00

USPC ......................................................... 514/248
See application file for complete search history.

(56) References Cited

U.S. PATENT DOCUMENTS 5,543,410 A 8/1996 Minin et al.

FOREIGN PATENT DOCUMENTS

| CA | 2966671 | 6/2016 |
|---|---|---|
| CN | 107567437 | 1/2018 |
| CN | 109563052 | 4/2019 |
| EP | 3248602 A1 | 11/2017 |
| JP | H 7-179431 | 7/1995 |
| JP | 2013-521239 | 6/2013 |
| JP | 2017-537958 | 12/2017 |
| JP | 2019-509268 | 4/2019 |
| KR | 10-20-13-0019383 | 2/2013 |
| RU | 2003130984 A | 4/2005 |
| RU | 2345774 C2 | 2/2009 |
| WO | 2016096143 | 6/2016 |
| WO | WO-2017/140430 A1 | 8/2017 |

OTHER PUBLICATIONS

Nikitin, A. A. et al.; "Search for Potent Modulators of Cytokine Production by Macrophages"; Bulletin of Experimental Biology and Medicine; vol. 138 No. 3; Sep. 2004; pp. 259-261.

Kubo, S. et al.; "Cytokine and chemokine expression in cigareet smoke-induced lung injury in guinea pigs"; European Respiratory Journal; vol. 26 No 6; Dec. 2005; pp. 993-1001.

"International Search Report"; prepared for application No. PCT/EP2021/000012; Authorized Officer Ulf Büttner; May 19, 2021; 4 pages.

*Primary Examiner* — Charanjit Aulakh
(74) *Attorney, Agent, or Firm* — Jackson Walker LLP

(57) ABSTRACT

The present invention relates to the use of 5-amino-2,3-dihydro-1,4-phthalazinedione or one of its pharmaceutically acceptable salts in the treatment of rare chronic inflammatory pulmonary diseases. The invention in particular relates to the use of 5-amino-2,3-dihydro-1,4-phthalazinedione sodium salt for said purposes.

22 Claims, 3 Drawing Sheets

1

Figure 1:
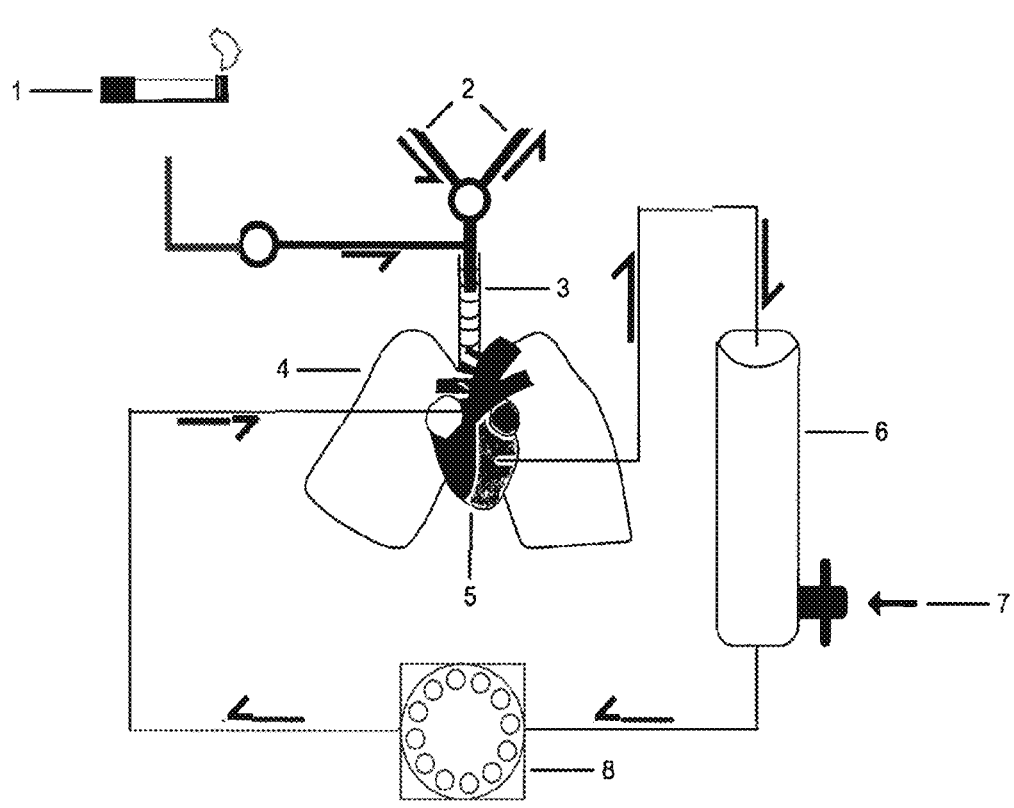

USE OF 5-AMINO-2,3-DIHYDRO-1,4-PHTHALAZINE-DIONE IN THE TREATMENT OF RARE CHRONIC INFLAMMATORY PULMONARY DISEASES

The present invention relates to the use of 5-amino-2,3-dihydro-1,4-phthalazinedione or its pharmaceutically acceptable salts in the treatment of rare chronic inflammatory pulmonary diseases. The invention in particular relates to the use of 5-amino-2,3-dihydro-1,4-phthalazinedione sodium salt for said purposes.

BACKGROUND OF THE INVENTION

Pulmonary diseases cover a plethora of diseases of the lower airways of the respiratory system, in particular of the lungs. While for common pulmonary diseases such as pneumonia, asthma or chronic obstructive pulmonary disease (COPD) pharmaceutical therapies are available there is a broad spectrum of rare chronic pulmonary diseases for which no effective or only a poorly effective medication has been developed yet. Because of economic prospects these rare diseases are not in the focus of the pharmaceutical industry. Thus, there is a medical need to provide pharmaceutical medications for the treatment of these rare chronic pulmonary diseases for patients in need thereof. Most of these rare chronic pulmonary diseases are classified in the ICD-10 Chapter X: Diseases of the respiratory system (J00-J99), Version 2016, as of Jan. 10, 2020.

The terms rare disease and orphan disease are often used synonymously. However, rare disease refers rather to the epidemiologic prevalence of a disease in a population. Orphan disease refers to the regulatory classification of a disease by the respective medical authorities. An orphan disease must be a rare disease and no effective medication is available due to a lack of economic incentive for the pharmaceutical industry (cf. Orphan Drug Act, USA; European Organization for Rare Diseases (EURORDIS)).

The term prevalence refers to the overall percentage of a population suffering from this specific disease. The term incidence refers to the number of new patients that become diseased with this specific disorder in the course of one year.

The frequency for such a classification may differ between countries, regions and ethnic groups. The frequency may also vary over time. For example, in the European Union a prevalence of 1:2000 or less is required, while in the USA a frequency of 1:1500 or less is required and in Japan a frequency of 1:2500 or less. In the scope of the present application the term rare disease(s) shall thus refer to a worldwide prevalence of 1:1500 or less.

The term pulmonary disease(s) encompasses pathological conditions that impair the gas exchange in the lungs or bronchi in mammals. In general, they are differentiated into obstructive and restrictive pulmonary diseases. Obstructive pulmonary diseases are characterized by airway obstruction. This limits the amount of air that is able to enter the alveoli because of constriction of the bronchial tree, due to inflammation. Restrictive pulmonary diseases are characterized by a loss of lung compliance, causing incomplete lung expansion and increased lung stiffness.

They can be also categorized as airway diseases, lung tissue diseases, lung infectious diseases and lung proliferative diseases. Airway diseases affect the tubes that carry oxygen and other gases into and out of the lungs. They usually cause a narrowing or blockage of the airways. Typical airway diseases include asthma, chronic obstructive pulmonary disease (COPD) and bronchiectasis. Lung tissue diseases affect the structure of the lung tissue. Scarring or inflammation of the tissue makes the lungs unable to expand fully. This complicates the gas exchange. As a result, these patients can't breathe deeply. Pulmonary fibrosis and sarcoidosis are typical examples thereof. Lung infectious diseases refer to disorders caused by an infection of the lower airways, e.g. pneumonia. Lung proliferative diseases include all tumors or neoplasms of the lower airways.

Most of the airway diseases are caused by an underlying inflammation or at least include an inflammatory component. Lung tissue diseases often also have an inflammatory component, unless they are caused by direct physical impairment of the respiratory tract. Infectious and proliferative diseases of the lungs may also have an inflammatory component, often secondary to the infection or the underlying malignancy.

Thus, these inflammatory pulmonary diseases have in common that they could be pharmacologically treated by anti-inflammatory drugs. While there are established medications for the treatment of acute inflammatory pulmonary diseases, e.g. for bacterial and viral infections, and of tumors there is still a need for pharmaceutical treatment of chronic inflammatory pulmonary diseases, in particular for the rare diseases of this group.

Thus, there is a medical need to find a pharmaceutical agent that shows a high efficacy in the treatment of rare chronic inflammatory pulmonary diseases.

Surprisingly, this task is solved by the administration of 5-amino-2,3-dihydro-1,4-phthalazinedione or one of its pharmaceutically acceptable salts or solvates, hydrates, crystalline polymorphs, tautomers or isotopically enriched forms thereof.

DETAILED DESCRIPTION OF THE INVENTION 5-amino-2,3-dihydro-1,4-phthalazinedione belongs to the pharmaceutical class of the phthalazinediones. Compounds of this class are known for their beneficial anti-inflammatory action. 5-amino-2,3-dihydro-1,4-phthalazinedione is also known under the name luminol. Luminol has excellent chemiluminescent properties. It is widely applied in diagnostic assays as a detection means and in forensic medicine, for example for tracing blood spots. In medicine, 5-amino-2,3-dihydro-1,4-phthalazinedione has been developed in the form of a sodium salt. In some countries it is approved for a broad range of acute and chronic inflammatory disorders, including a.o. acute infections of bacterial and viral origin, particularly of the intestinal tract, hepatitis B and C, gastroenteritis, inflammations such as prostatitis, endometriosis, throat inflammation, bronchial asthma, pneumonia, periodontitis, pyelonephritis and autoimmune diseases such as Crohn's disease, ulcerative colitis, lupus erythematosus and scleroderma. Further, there is still a long list of indications in scientific and patent literature in the treatment of which 5-amino-2,3-dihydro-1,4-phthalazinedione sodium salt was allegedly tested or a beneficial use was suggested (cf. WO 2004/041169; WO 2007/018546; WO 2012/127441; WO 2017/202496; WO 2018/082814: a.o.).

While most conventional immunomodulatory drugs show serious adverse reactions, or are at least problematic in long-term treatment, 5-amino-2,3-dihydro-1,4-phthalazinedione and its pharmaceutically acceptable salts are well tolerated and have a high safety margin in respect to administered dosages.

To ensure a better solubility and bioavailability pharmaceutically acceptable salts of 5-amino-2,3-dihydro-1,4- phthalazinedione are used. Sodium, potassium and lithium salts have been described for therapeutic applications (cf. WO 2010/082858). Crystal structures for lithium, sodium, potassium, rubidium and cesium salts were described in Guzei et al. (2013) *Journal of Coordination Chemistry* 66, 3722-3739. Thus, the present patent application refers also to the use of all pharmaceutically acceptable salts of 5-amino-2,3-dihydro-1,4-phthalazinedione.

5-amino-2,3-dihydro-1,4-phthalazinedione is often used as a hydrate, for example as sodium salt dihydrate. Thus, the present patent application refers also to the use of all hydrates and other solvates of 5-amino-2,3-dihydro-1,4-phthalazinedione and its pharmaceutically acceptable salts. 5-amino-2,3-dihydro-1,4-phthalazinedione or one of its pharmaceutically acceptable salts may build complexes with suitable ligands. Thus, the present patent application refers also to such complexes.

Thus, the present application refers to 5-amino-2,3-dihydro-1,4-phthalazinedione or one of its pharmaceutically acceptable salts for use in the prophylaxis or treatment of a chronic inflammatory pulmonary disease, wherein said chronic inflammatory pulmonary disease has a worldwide prevalence of 1:1500 or less. Preferred is 5-amino-2,3-dihydro-1,4-phthalazinedion sodium salt.

In particular, the disclosure refers also to a worldwide prevalence of 1:1700 or less, or 1:2000 or less, or 1:2500 or less, or 1:3000 or less, or 1:4000 or less, or 1:5000 or less, or 1:6000 or less, or 1:7000 or less, or 1:8000 or less, or 1:9000 or less, or 1:10000 or less.

Alternatively, the disclosure refers also to a worldwide prevalence in the range of 1:1500 to 1:2000000, or 1:1700 to 1:2000000, or 1:2000 to 1:2000000, or 1:2500 to 1:2000000, or 1:3000 to 1:2000000, or 1:4000 to 1:2000000, or 1:5000 to 1:2000000, or 1:6000 to 1:2000000, or 1:7000 to 1:2000000, or 1:8000 to 1:2000000, or 1:9000 to 1:2000000, or 1:10000 to 1:2000000.

In order to ensure a reproducible and standardized API production and to provide improved stability features of an active agent anhydrous formulations are often preferred. Anhydrate forms of 5-amino-2,3-dihydro-1,4-phthalazinedione sodium salt have been described as crystalline polymorphs in WO 2011/107295 (Form I, Form II) and WO 2016/096143 (Form III). These crystalline polymorphs are virtually free from phase impurities and were characterized by means of X-ray powder diffraction. This method yields a set of characteristic d-values indicating interplanar spacings [Å] and of the corresponding 2-theta (2θ) angles [°] under which Bragg reflections occur. This yields a unique and unambiguous fingerprint of the respective polymorphs.

For Form I the following values were determined:
d values: 13.5; 6.9; 5.2; 4.6; 3.9; 3.5; 3.4; 3.3; 3.1; 3.0 and/or
2-theta values: 6.5; 12.7; 16.9; 19.3; 22.8; 25.8; 26.6; 27.2; 28.7; 30.3.
Form II is characterized by the following values:
d values: 12.9; 7.9; 7.1; 6.5; 5.3; 4.0; 3.7; 3.6; 3.3; 3.2 and/or
2-theta values: 6.8; 11.2; 12.5; 13.7; 16.7; 22.4; 24.3; 24.9; 27.2; 27.8.
Form III yielded the following values:
d values: 13.131; 7.987; 7.186; 6.566; 6.512; 5.372; 3.994; 3.662; 3.406; 3.288; 3.283; 3.222; 3.215; 3.127; 2.889 and/or
2-theta values: 6.73; 11.07; 12.31; 13.48; 13.59; 16.49; 22.24; 24.29; 26.14; 27.10; 27.14; 27.67; 27.72; 28.52; 30.93.

5-amino-2,3-dihydro-1,4-phthalazinedione itself shows also polymorphism. A Form I (Paradies (1992) *Ber. Bunsen-Ges. Phys. Chem* 96: 1027-1031) and a Form II (WO 2017/140430) have been disclosed.

Thus, the present patent application refers also to the use according to the invention of all crystalline forms and polymorphs thereof of 5-amino-2,3-dihydro-1,4-phthalazinedione or of one of its pharmaceutically acceptable salts.

Similar therapeutic effects are known for a variety of phthalazinediones, respectively of derivatives of 5-amino-2,3-dihydro-1,4-phthalazinedione and its pharmaceutically acceptable salts. An example is 6-amino-2,3-dihydrophthalazine-1,4-dione (isoluminol). An overview of suitable phthalazinediones is given in WO 2007/018546. It is reasonable to assume that these compounds show comparable effects when being used for the therapeutic applications according to the invention.

Tautomerism relates to a rapid intraconversion of organic compounds in which a hydrogen atom or proton formally migrates inside the compound. This is accompanied by a switch of a single bond and adjacent double bond. The single forms are called tautomers. For example, keto-enol tautomerism occurs in 5-amino-2,3-dihydro-1,4-phthalazinedione (Proescher and Moody (1939) *J Lab Clin Med,* 1183-1189). Thus, the present patent application refers also to the use of all tautomers of 5-amino-2,3-dihydro-1,4-phthalazinedione and its pharmaceutically acceptable salts.

Isomer is a generic term for molecules with the same chemical formula but a different chemical structure. They can be differentiated into constitutional (structural) isomers (wherein an exchange of atoms or of a functional group occurs) and stereoisomers. Stereoisomers can be subdivided into enantiomers (non-superimposable mirror images of the same molecule) and diastereomers (the same molecule with a different configuration at one or more stereocenters). Diastereomers can be subdivided into cis/trans isomers (referring to the relative orientation of functional groups within a molecule) and on the other hand conformers (rotation about formally single bonds) and rotamers (different rotational positioning about a single bond). An example for a constitutional isomer of 5-amino-2,3-dihydro-1,4-phthalazinedione is 6-amino-2,3-dihydrophthalazine-1,4-dione (isoluminol). Stereoisomers may occur in phthalazinedione derivatives. Thus, the present patent application refers also to the use of all isomers of 5-amino-2,3-dihydro-1,4-phthalazinedione, its derivatives and pharmaceutically acceptable salts.

For some applications it may be desirable that isotopically enriched forms of the compounds of the invention are used, e.g. for diagnostic purposes. Thus, the present patent application refers also to such isotopically enriched forms of the compounds of the invention.

From a pharmacokinetic point of view or for a production rationale it may be preferable to use a prodrug as a dosage form. A prodrug is administered in a pharmacologically inactive form and is metabolically converted into the active form inside the body. This conversion may occur systemically or locally. Thus, the present patent application refers also to prodrugs of the compounds of the invention.

As used throughout the present application the term "5-amino-2,3-dihydro-1,4-phthalazinedione or one of its pharmaceutically acceptable salts" shall encompass all the aforementioned molecular variants of 5-amino-2,3-dihydro-1,4-phthalazinedione, i.e. 5-amino-2,3-dihydro-1,4-phthalazinedione or one of its pharmaceutically acceptable salts or solvates, hydrates, crystalline polymorphs, tautomers or isotopically enriched forms thereof.

Unless otherwise stated, any technical or scientific term used in the present invention has the meaning that a man skilled in the relevant technical art will attribute to them.

According to the application the terms "drug substance", "active substance", "active agent", "pharmaceutically active agent", "active ingredient" or "active pharmaceutical ingredient" (API) refer to 5-amino-2,3-dihydro-1,4-phthalazinedione or its pharmaceutically acceptable salts, if not stated otherwise or used in a general sense.

The terms "composition" or "pharmaceutical composition" comprise at least one active ingredient in any pharmacologically acceptable defined dosage and dosage form together with at least one pharmaceutically acceptable excipient, as well as all agents that are generated from the ingredients as outlined below directly or indirectly as a combination, accumulation, complex or crystal, or as a consequence of other reactions or interactions, as well as optionally at least one further pharmaceutical drug, as listed below.

The term "excipient" is used in this application to describe any component of a pharmaceutical composition apart of the pharmaceutically active principle. The selection of suitable excipients depends on a variety of factors, such as the dosage form, the dosage, the desired solubility and the stability of the composition.

The terms "effect", "therapeutic effect", "action", "therapeutic action", "efficacy" and "effectiveness" in regard to the substance of the invention or any other active substance mentioned in the description refers to causally occurring beneficial consequences in the organism to which said substance has been administered before.

According to the invention the terms "effective amount" and "therapeutically effective amount" refer to an amount of the substance of the invention that is sufficiently large to cause a desired beneficial effect in a subject in need of such a treatment.

The terms "treatment" and "therapy" comprise the administration of at least the substance of the invention, alone or in combination with at least one further pharmaceutical drug, independently of the chronological order of the administration. Such an administration is intended to substantially improve the disease course of a chronic inflammatory pulmonary disease having a worldwide prevalence of 1:1500 or less by either completely curing the disease or by stopping or decelerating the increase of disabilities during the course of the disease.

The terms "prophylaxis" or "prophylactic treatment" comprise the administration of at least the substance of the invention, alone or in combination with at least one further pharmaceutical drug, independently of the chronological order of the administration, in order to prevent or suppress the manifestation of symptoms attributed to a chronic inflammatory pulmonary disease having a worldwide prevalence of 1:1500 or less. It refers in particular to medical conditions of a patient in which the manifestation of such symptoms is expected to occur in the far or near future with a reasonable probability.

The terms "subject" and "patient" comprise individuals suffering from disease symptoms or disabilities related to a chronic inflammatory pulmonary disease having a worldwide prevalence of 1:1500 or less wherein said diagnosis is either approved or suspected. Individuals are mammals, in particular humans.

In the scope of the present application the term "medicine" shall comprise human and veterinary medicine.

In the sense of the present patent application the terms "inflammatory diseases" or "inflammatory pulmonary diseases" refer to diseases, disorders or other body conditions in which an inflammation, in particular of the lungs, becomes manifest as a major symptom. An inflammation is the response of body tissues to irritation (exogenous or endogenous noxae) or injury. It can be provoked amongst others by physical, chemical and biologic stimuli, comprising mechanical trauma, radiation damage, corrosive chemicals, extremes of heat or cold, infectious agents such as bacteria, viruses, fungi and other pathogenic microorganisms or parts of them. An inflammation can have beneficial (e.g. within the scope of wound healing) and/or detrimental effects in the affected tissue(s). At a first stage an inflammation is regarded as acute. When it isn't terminated after some time the inflammation may become chronic. Typical signs of an inflammation are redness, swelling, heat development, pain and reduced functionality. This may even lead to a loss of function of the affected tissue.

An inflammation is one of the first responses of the immune system that has become activated e.g. by an infection or degenerated endogenous cells. The system of innate immunity mediates an unspecific response, amongst others a general inflammatory response, while the adaptive immune system provides reactions specific to the respective pathogen, which will then be remembered by the immune system. An organism can be in an immunodeficient state, i.e. the immune response is not able to cope with the aforementioned irritations or injuries in a satisfactory manner. On the other hand, the immune system might become hyperactive and turn its defense against endogenous tissues, as in the case of autoimmune diseases.

In the sense of the present patent application the terms "degenerative diseases" or "degenerative pulmonary diseases" refer to diseases, disorders or other body conditions in which a continuous process leads to degenerative cell changes. The affected tissues or organs deteriorate continuously over time. Such a degeneration may be due to physical or physiological over-exercise of specific vulnerable body structures, lifestyle, eating habits, age, congenital diseases or other endogenous causes. The degeneration can be caused or accompanied by an atrophy or dystrophy of the respective tissue or organ, especially the lungs. Often a loss of function and/or an irreversible damage of the affected tissue or organ occurs.

In the sense of the present patent application the terms "lesion", "microlesion" and "trauma" refer to injuries of different size and scope in the affected pulmonary tissue. They can be inflicted by spontaneous physical impact in which the impacting force or torque leads to a tissue damage. But they can also be the final consequence of a previous degenerative disease of the affected pulmonary tissue, or vice versa a microlesion may be the starting point of such a degenerative disease in the wake of the microlesion. Also an inflammation of the affected pulmonary tissue can favor such a microlesion or trauma, or it can be their sequelae. So these terms are interconnected with inflammation and degenerative disease.

In the sense of the present patent application the term "primary" disease, as e.g. a "primary inflammatory or degenerative disease" refers to pulmonary diseases which are not autoimmune-mediated.

If it is known that a healthy person is or will be vulnerable to inflammatory or degenerative diseases, or a tissue damage is to be expected due to a constant overstrain of the respective tissue or organ it can be indicated to give a prophylactic medication in order to prevent or at least to mitigate the expected impairment or damage. Thus, the present patent application refers also to a prophylactic use according to the invention.

There are also cases in which an inflammatory pulmonary disease results in a degenerative disease. Examples therefore will be given further below. Thus, the present patent application refers to the use according to the invention in the prophylaxis or treatment of inflammatory and/or degenerative pulmonary diseases, particularly in the treatment of primary inflammatory and/or degenerative pulmonary diseases.

In the scope of the present application the term "pulmonary" refers to organs and tissues of the lower respiratory tract. Examples of organs and tissues of the lower respiratory tract are, without being limiting, the lungs including their lobes, apices, lingulae and alveoli; the bronchi including respiratory bronchioles; tracheal and bronchi rings including the carina; pulmonary vessels including lung vessels and bronchial vessels and bronchial vessels; bronchopulmonary lymph nodes; autonomous nervous system of the lung;

In the scope of the present application the "pulmonary" further refers to adjacent organs and tissues that functionally or structurally are closely linked to the lower respiratory tract and/or the thorax and therefore can be pharmaceutically accessed excellently by inhalation. Examples are, without being limiting, pleura and diaphragm.

In the scope of the present application the terms "alveoli" and "alveolar" refer to the tissue structures at the bottom of the lung airways. Alveoli are hollow cup-shaped cavities found in the lung parenchyma where gas exchange takes place. Further, they are located sparsely on the respiratory bronchioles, line the walls of the alveolar ducts, and are more numerous in the blind-ended alveolar sacs. The alveolar membrane is the gas exchange surface, surrounded by a network of capillaries. Across the membrane oxygen is diffused into the capillaries and carbon dioxide released from the capillaries into the alveoli to be breathed out. Alveoli consist of an epithelial layer of simple squamous epithelium and an extracellular matrix surrounded by capillaries. The epithelial lining is part of the alveolar membrane, also known as the respiratory membrane.

Type I and type II pneumocytes are found in the alveolar wall. Alveolar macrophages are immune cells that move about in the alveolar lumen and in the connective tissue between them. Type I cells are squamous epithelial cells, thin and flat and form the structure of the alveoli. Type II cells (goblet cells) release pulmonary surfactant to lower surface tension.

A typical pair of human lungs contain about 300 million alveoli, producing 70 $m^2$ of surface area. Each alveolus is wrapped in a fine mesh of capillaries covering about 70% of its area. The diameter of a typical healthy alveolus is between 200 and 500 µm.

There is no generally accepted time limit after which a disease, respectively its symptoms, have to be regarded as chronic. In the art, this point in time differs between four weeks and six months. A good compromise are three months (cf. Bernell and Howard (2016) *Frontiers in Public Health* 4: 159). In the scope of the present application the term chronic shall refer therefore to diseases, respectively symptoms that persist for more than three months. The term chronic shall also encompass chronic recurrent, respectively relapsing diseases. It shall further also encompass chronic progredient diseases.

Further, there are inflammatory pulmonary diseases or conditions that start with a strong acute phase but bear the risk to become chronic, either idiopathically or by lack of effective treatment. At the beginning of a pharmaceutical treatment it can't be predicted whether an acute treatment will be sufficient, or a permanent treatment will be needed. Examples for such diseases are the postprocedural inflammatory pulmonary diseases according to the invention, e.g. after a lung surgery. In the scope of the present application this group of diseases shall be encompassed in the class of chronic inflammatory pulmonary diseases.

In Example 1 an ex vivo mouse lung was exposed over 5 minutes to cigarette smoke. Cigarette smoke is known to contain a plethora of cytotoxic agents that a.o. lead to a drastic intracellular increase of reactive oxygen species (ROS) and reactive nitrogen species (RNS) in the affected lung tissue. ROS/RNS are known to cause multiple cellular damages such as radical formation of further cellular molecules, peroxide formation, lipid peroxidation, damage of the cell membrane and intracellular membranes, DNA damages, unwanted protein modifications and induction of apoptosis. On the other hand, they are key mediators for initiating an immune response that helps the cell, respectively the tissue or the whole organism to cope with xenobiotics (e.g. toxins from cigarette smoke) and infections. The problem is an overshooting immune reaction that causes the aforementioned symptoms of an acute or chronic inflammation. Therefore it is generally acknowledged that the reduction of excessive intracellular ROS/RNS levels is a promising approach for an anti-inflammatory therapy in general. Specifically, this also holds true for inflammatory pulmonary diseases. Hence the ex vivo lung model used in Example 1 is not only indicative for therapeutic efficacy in pulmonary diseases caused by cigarette smoke such as COPD but for all inflammatory pulmonary diseases.

The administration of 5-amino-2,3-dihydro-1,4-phthalazinedione sodium salt to this cigarette smoke-stimulated mouse lung showed a dose-dependent reduction of ROS/RNS levels down to control levels before cigarette smoke exposition. This proves that 5-amino-2,3-dihydro-1,4-phthalazinedione and in particular 5-amino-2,3-dihydro-1,4-phthalazinedione sodium salt has a huge potential for prophylactic and therapeutic efficacy in inflammatory pulmonary diseases.

The chronic inflammatory pulmonary diseases having a worldwide prevalence of 1:1500 or less can be classified as follows:

a) Chronic lower respiratory diseases

These diseases comprise, without being limiting, bronchiectasis; pulmonary alveolar microlithiasis.

b) Lung diseases due to an external agent

These diseases comprise, without being limiting, coalworker's pneumoconiosis; asbestosis; pneumoconiosis due to talc dust; silicosis; aluminosis of lung; bauxite fibrosis of lung; berylliosis; graphite fibrosis of lung; siderosis; stannosis; pneumoconiosis due to other specified inorganic dusts; unspecified pneumoconiosis; pneumoconiosis associated with tuberculosis; byssinosis; flax-dresser's disease; cannabinosis; airway disease due to other specific organic dusts; farmer's lung; bagassosis; bird fancier's lung; suberosis; maltworker's lung; mushroom-worker's lung; maplebark-stripper's lung; air-conditioner and humidifier lung; hypersensitivity pneumonitis due to other organic dusts such as cheese-washer lung, coffee-worker lung, fishmeal-worker lung, furrier lung and sequiosis; hypersensitivity pneumonitis due to unspecified organic dust such as allergic alveolitis and hypersensitivity pneumonitis; respiratory conditions due to inhalation of chemicals, gases, fumes and vapors; pneumonitis due to solids and liquids; radiation pneumonitis; fibrosis of lung following radiation; acute drug-induced interstitial lung disorders; chronic drug-induced interstitial lung disorders; drug-induced interstitial lung disorders, unspecified; respiratory conditions due to other specified external agents; respiratory conditions due to unspecified external agent.

c) Respiratory diseases principally affecting the interstitium

These diseases comprise, without being limiting, pulmonary permeability edema; high-altitude pulmonary edema; eosinophilic asthma; Löffler's pneumonia; tropical pulmonary eosinophilia; alveolar and parietoalveolar conditions; Hamman-Rich syndrome; other specified interstitial pulmonary diseases; interstitial pulmonary disease, unspecified.

d) Suppurative and/or necrotic conditions of lower respiratory tract

These diseases comprise, without being limiting, abscess of lung with pneumonia, pyothorax.

e) Pleura diseases

These diseases comprise, without being limiting, pleural plaque; pneumothorax; chylothorax; fibrothorax; hemothorax; hemopneumothorax; hydrothorax; pleural condition, unspecified.

f) Postprocedural or related lower respiratory diseases

These diseases comprise, without being limiting, chronic pulmonary insufficiency following surgery; host-versus-graft disease after lung transplantation; graft-versus-host disease after lung transplantation; chronic lung allograft dysfunction (CLAD), chronic lung allograft dysfunction—bronchiolitis obliterans syndrome (CLAD-BOS); lung ischemia reperfusion injury; primary graft dysfunction after lung transplantation; Mendelson's syndrome; other postprocedural respiratory disorders; postprocedural respiratory disorder, unspecified; respiratory failure, not elsewhere classified; diseases of bronchus, not elsewhere classified; pulmonary collapse; atelectasis; interstitial emphysema; mediastinal emphysema; compensatory emphysema; mediastinitis; disorders of diaphragm.

g) Pulmonary diseases specific to the perinatal period

These diseases comprise, without being limiting, transient tachypnoea of newborn; congenital pneumonia due to viral agent; congenital pneumonia due to *Chlamydia; congenital pneumonia due to Staphylococcus*; congenital pneumonia due to *Streptococcus*, group B; congenital pneumonia due to *Escherichia coli*; congenital pneumonia due to *Pseudomonas*; congenital pneumonia due to bacterial agents such as *Haemophilus influenzae, Klebsiella pneumoniae, Mycoplasma, Streptococcus*, except group B; congenital pneumonia due to other organisms; congenital pneumonia, unspecified; neonatal aspiration of meconium; interstitial emphysema originating in the perinatal period; pneumothorax originating in the perinatal period; pneumomediastinum originating in the perinatal period; other conditions related to interstitial emphysema originating in the perinatal period; pulmonary hemorrhage originating in the perinatal period; Wilson-Mikity syndrome; unspecified chronic respiratory disease originating in the perinatal period.

In detail, the present application refers to 5-amino-2,3-dihydro-1,4-phthalazinedione or one of its pharmaceutically acceptable salts for use in the prophylaxis or treatment of a chronic inflammatory pulmonary disease by inhalatory administration, wherein the chronic inflammatory pulmonary disease is selected from the group chronic lower respiratory diseases, lung diseases due to an external agent, respiratory diseases principally affecting the interstitium, suppurative and/or necrotic conditions of lower respiratory tract, pleura diseases, postprocedural or related lower respiratory diseases and pulmonary diseases specific to the perinatal period.

In particular, the present application refers to 5-amino-2,3-dihydro-1,4-phthalazinedione or one of its pharmaceutically acceptable salts for use in the prophylaxis or treatment of a chronic inflammatory pulmonary disease, wherein the chronic inflammatory pulmonary disease is a chronic lower respiratory disease.

In particular, the present application refers to 5-amino-2,3-dihydro-1,4-phthalazinedione or one of its pharmaceutically acceptable salts for use in the prophylaxis or treatment of a chronic inflammatory pulmonary disease, wherein the chronic inflammatory pulmonary disease is a lung disease due to an external agent.

In particular, the present application refers to 5-amino-2,3-dihydro-1,4-phthalazinedione or one of its pharmaceutically acceptable salts for use in the prophylaxis or treatment of a chronic inflammatory pulmonary disease, wherein the chronic inflammatory pulmonary disease is a respiratory diseases principally affecting the interstitium.

In particular, the present application refers to 5-amino-2,3-dihydro-1,4-phthalazinedione or one of its pharmaceutically acceptable salts for use in the prophylaxis or treatment of a chronic inflammatory pulmonary disease, wherein the chronic inflammatory pulmonary disease is a suppurative and/or necrotic condition of the lower respiratory tract.

In particular, the present application refers to 5-amino-2,3-dihydro-1,4-phthalazinedione or one of its pharmaceutically acceptable salts for use in the prophylaxis or treatment of a chronic inflammatory pulmonary disease, wherein the chronic inflammatory pulmonary disease is a pleura disease.

In particular, the present application refers to 5-amino-2,3-dihydro-1,4-phthalazinedione or one of its pharmaceutically acceptable salts for use in the prophylaxis or treatment of a chronic inflammatory pulmonary disease, wherein the chronic inflammatory pulmonary disease is a postprocedural or related lower respiratory disease.

In particular, the present application refers to 5-amino-2,3-dihydro-1,4-phthalazinedione or one of its pharmaceutically acceptable salts for use in the prophylaxis or treatment of a chronic inflammatory pulmonary disease, wherein the chronic inflammatory pulmonary disease is a pulmonary disease specific to the perinatal period.

In detail, the present disclosure refers to 5-amino-2,3-dihydro-1,4-phthalazinedione or one of its pharmaceutically acceptable salts for use in the prophylaxis or treatment of a chronic inflammatory pulmonary disease having a worldwide prevalence of 1:1500 or less, wherein said chronic inflammatory pulmonary disease is selected from a group consisting of bronchiectasis, pulmonary alveolar microlithiasis, coalworker's pneumoconiosis, asbestosis, pneumoconiosis due to talc dust, silicosis, aluminosis of lung, bauxite fibrosis of lung, berylliosis, graphite fibrosis of lung, siderosis, stannosis, pneumoconiosis associated with tuberculosis, byssinosis, flax-dresser's disease, cannabinosis, farmer's lung, bagassosis, bird fancier's lung, suberosis, maltworker's lung, mushroom-worker's lung, maple-bark-stripper's lung, air-conditioner lung, humidifier lung, cheese-washer lung, coffee-worker lung, fishmeal-worker lung, furrier lung, sequiosis, allergic alveolitis, hypersensitivity pneumonitis, respiratory conditions due to inhalation of chemicals, gases, fumes and vapors, pneumonitis due to solids and liquids, radiation pneumonitis, fibrosis of lung following radiation, chronic drug-induced interstitial lung disorders, pulmonary permeability edema, high-altitude pulmonary edema, eosinophilic asthma, Löffler's pneumonia, tropical pulmonary eosinophilia, alveolar and parietoalveolar conditions, Hamman-Rich syndrome, abscess of lung with pneumonia, pyothorax, pleural plaque, pneumothorax, chylous effusion, fibrothorax, hemothorax, hemopneumothorax, hydrothorax, chronic pulmonary insufficiency following surgery, host-versus-graft disease after lung transplantation, graft-versus-host disease after lung transplantation, chronic lung allograft dysfunction, chronic lung allograft dysfunction—bronchiolitis obliterans syndrome, lung ischemia reperfusion injury, primary graft dysfunction after lung transplantation, Mendelson's syndrome, pulmonary collapse, atelectasis, interstitial emphysema, mediastinal emphysema, compensatory emphysema, mediastinitis, disorders of diaphragm, transient tachypnoea of newborn, congenital pneumonia due to viral agent, congenital pneumonia due to *Chlamydia*, congenital pneumonia due to *Staphylococcus*, congenital pneumonia due to *Streptococcus* group B, congenital pneumonia due to *Escherichia coli*, congenital pneumonia due to *Pseudomonas*, congenital pneumonia due to *Haemophilus influenzae*, congenital pneumonia due to *Klebsiella pneumoniae*, congenital pneumonia due to *Mycoplasma*, neonatal aspiration of meconium, interstitial emphysema originating in the perinatal period, pneumothorax originating in the perinatal period, pneumomediastinum originating in the perinatal period, pulmonary hemorrhage originating in the perinatal period, and Wilson-Mikity syndrome.

In the scope of the present application also bronchiectasis is of particular interest. Bronchiectasis is believed to be an idiopathic disease. Morphologically, it is characterized by a permanent enlargement of parts of the lower airways. As pathologic conditions, a.o. post-infection, immune deficiency, exaggerated immune response, congenital abnormalities, inflammatory pneumonitis, fibrosis and mechanical obstruction are discussed. Symptoms include chronic cough along with daily production of mucus. Thus, it resembles cystic fibrosis, but without the characteristic gene mutation. Pulmonary function testing results generally show airflow obstruction ranging from moderate to severe. Additional symptoms include dyspnea, coughing up blood, chest pain, hemoptysis, fatigue, and weight loss.

Treatment of bronchiectasis aims at controlling infections and bronchial secretions, relieving airway obstructions, removal of affected portions of lung by surgery or artery embolization. If indicated, antibiotics, in particular macrolide antibiotics are administered. Mucus overproduction can be addressed by mucolytics. Bronchodilators are used for facilitating breathing. Continuous inhaled corticosteroids help to some extent to reduce sputum production, to decrease airway constriction and to prevent disease progression.

Thus, the present application refers also to 5-amino-2,3-dihydro-1,4-phthalazinedione or one of its pharmaceutically acceptable salts in the prophylaxis or treatment of bronchiectasis.

A typical chronic inflammatory disease having a worldwide prevalence of 1:1500 or less that is caused by an external agent is berylliosis (interchangeably herein, chronic beryllium disease, CBD). There is no cure for this occupational disease, only symptomatic treatment.

Prolonged exposure by inhalation may sensitize the lungs to beryllium, leading to the development of small inflammatory nodules, called granulomas. Typically, CBD granulomas are not characterized by necrosis and therefore not exhibiting a caseating appearance. Ultimately, this process leads to a decrease in pulmonary diffusion capacity. The typical symptoms are cough and dyspnea. Other symptoms include chest pain, joint aches, weight loss, and fever. The patient's T-cells become sensitized to beryllium. The pathologic immune response leads to an accumulation of CD4+ helper T-lymphocytes and macrophages in the lungs. There they aggregate together and form granulomas. Eventually, this leads to lung fibrosis. Treatment options include oxygen application and orally administered corticosteroids.

Thus, the present application refers also to 5-amino-2,3-dihydro-1,4-phthalazinedione or one of its pharmaceutically acceptable salts for use in the prophylaxis or treatment of berylliosis.

In the scope of the present application also chronic lung allograft dysfunction is of particular interest. Chronic lung allograft dysfunction (CLAD), respectively chronic lung allograft dysfunction—bronchiolitis obliterans syndrome (CLAD-BOS) is a major problem in the long-term management of lung transplant recipients. Both alloimmune-dependent factors (rejection) and alloimmune-independent factors contribute to the development of CLAD. It encompasses all forms of chronic pulmonary function decline, after eliminating known causes (persistent acute rejection, infection, anastomotic stricture, or disease recurrence, pleural disease, diaphragm dysfunction or native lung hyperinflation). Therefore, it is a heterogeneous entity in which two main phenotypes are currently identified: Bronchiolitis obliterans syndrome (BOS), defined by a persistent decline in FEV1, and an obstructive functional pattern.

No treatment is currently available to reverse CLAD after diagnosis. Pharmaceutical treatment of the symptoms is carried out with azithromycin (first line), alternatively montelukast. In therapy-resistant cases photopheresis is applied.

Thus, the present application refers also to 5-amino-2,3-dihydro-1,4-phthalazinedione or one of its pharmaceutically acceptable salts for use in the prophylaxis or treatment of CLAD, respectively CLAD-BOS.

In the scope of the present application also pulmonary edema is of particular interest. Pulmonary edema may have different causes. Fluid accumulation occurs in the tissue and air spaces of the lungs, leading to impaired gas exchange and in the worst case to respiratory failure. Therapy for pulmonary edema focusses mainly on maintaining vital functions, e.g. by tracheal intubation and mechanical ventilation. Hypoxia symptoms can be addressed by oxygen supplementation Pulmonary permeability edema is characterized by reduced alveolar $Na^+$ uptake capacity and capillary barrier dysfunction and is a potentially lethal complication, e.g. in listeriosis induced by listeriolysin. Apical $Na^+$ uptake is mainly mediated by the epithelial sodium channel (ENaC) and initiates alveolar liquid clearance.

High-altitude pulmonary edema (HAPE) occurs in otherwise healthy people at altitudes typically above 2,500 meters and can be life-threatening. After a rapid gain in altitude, symptoms may include shortness of breath at rest, cough, weakness or decreased exercise performance, chest tightness or congestion, crackles or wheezing, central blue skin color, tachypnea and tachycardia. The lower air pressure at high altitudes leads to a decrease in partial pressure of arterial oxygen. Due to hypoxemia pulmonary hypertension secondary to hypoxic pulmonary vasoconstriction and increased capillary pressure develop. This leads to subsequent leakage of cells and proteins into the alveoli. Hypoxic pulmonary vasoconstriction occurs diffusely, leading to arterial vasoconstriction in all areas of the lung.

The first medical measure is a descent to a lower altitude as quickly as possible. Alternatively, oxygen supplementation for maintaining an $S_{po2}$ above 90% is possible.

Pharmaceutical prophylaxis of HAPE includes calcium channel blockers such as nifedipine, PDE5 inhibitors such as sildenafil and tadalafil and inhaled beta 2-agonists such as salmeterol.

A new pharmaceutical approach to enhance ENaC function is e.g. the peptide drug solnatide.

Thus, the present application refers also to 5-amino-2,3-dihydro-1,4-phthalazinedione or one of its pharmaceutically acceptable salts for use in the prophylaxis or treatment of pulmonary permeability edema and high-altitude pulmonary edema.

In the scope of the present application also lung ischemia reperfusion injury is of particular interest. In lung transplantation, organ ischemia and subsequent reperfusion is unavoidable and commonly leads to acute, sterile inflammation after transplant called ischemia-reperfusion (IR) injury. Severe IR injury leads to primary graft dysfunction (PGD), which is the major source of both short- and long-term morbidity and mortality after lung transplantation. Currently, there are no therapeutic agents clinically utilized to specifically prevent IR injury, and treatment strategies are limited to supportive care. If feasible, the donor lung, respectively the donor can be prophylactically treated with 5-amino-2,3-dihydro-1,4-phthalazinedione or one of its pharmaceutically acceptable salts.

Endothelial cell dysfunction and disruption of the endothelial barrier are hallmarks of lung IR injury. Depolarization of endothelial cell membranes induces ROS production and subsequent inflammation and leukocyte extravasation. Activation of NADPH oxidase (NOX2), induction of nitric oxide (NO) production, and activation of integrin $\alpha v \beta 5$, promote vascular permeability via ROS/RNS production. Alveolar macrophages are activated. Elevated chemokine levels and adhesion molecule expression on endothelial cells and neutrophils lead to binding and infiltration of neutrophils, which can release cytokines, ROS and form neutrophil extracellular traps (NETs).

Recent prophylactic strategies before lung transplantation include administration to the organ recipient of anti-oxidants (free radical scavengers) or inhibitors of oxidant-producing enzymes (e.g. methylene blue or N-acetylcysteine), anti-inflammatory strategies using inhibitors of pro-inflammatory transcription factors or inflammatory mediators, ventilation with gaseous molecules such as carbon monoxide or inhaled anesthetic sevoflurane, growth factors or dietary supplements such as creatine, as well as cell-based therapies such as application of mesenchymal stem cells.

Thus, the present application refers also to 5-amino-2,3-dihydro-1,4-phthalazinedione or one of its pharmaceutically acceptable salts for use in the prophylaxis or treatment of lung ischemia reperfusion injury.

In the scope of the present application also primary graft dysfunction after lung transplantation is of particular interest. Primary graft dysfunction (PGD) is a devastating form of acute lung injury that afflicts about 10% to 25% of patients in the first hours to days after lung transplantation. Clinically and pathologically it is a syndrome that mimics adult respiratory distress syndrome (ARDS) and carries a mortality of up to 50%. PGD can have different causes such as ischemia reperfusion injury described before, epithelial cell death, endothelial cell dysfunction, innate immune activation, oxidative stress, release of inflammatory cytokines and chemokines as well as iatrogenic factors such as mechanical ventilation and transfusion of blood components. Activation of the innate immune system activation has been demonstrated during the onset and spread of ischemia reperfusion injury. Herein PGD is associated with the innate immunity pathways of a Toll-like receptor-mediated injury.

Molecular markers of PGD include intracellular adhesion molecule-1, surfactant protein-1, plasminogen activator inhibitor, soluble receptor for advance glycation end products and protein C.

Approaches for avoiding PGD development include reperfusion optimization, regulation of prostaglandin levels, hemodynamic control, hormone replacement, ventilator management and donor lung preparation strategies. To decrease PGD incidence, strategies, such as using prostaglandins, nitric oxide, surfactant, adenosine or inhibition of pro-inflammatory mediators and/or elimination of free oxygen radicals, have been used. Furthermore, for the inhibition of neutrophils and neutrophil-borne mediators, free oxygen radicals, cytokines, proteases, lipid mediators, adhesion molecules and complement cascade inhibitors have been investigated. Inhaled nitric oxide may lower the pulmonary arterial pressure, without affecting the systemic blood pressure. As a last life-saving resort option, extracorporeal membrane oxygenation (ECMO) is used for correcting PGD-induced hypoxemia and by providing necessary gas exchange.

Thus, the present application refers also to 5-amino-2,3-dihydro-1,4- or one of its pharmaceutically acceptable salts for use in the prophylaxis or treatment of primary graft dysfunction after lung transplantation.

This also holds true for the aforementioned subtypes of inflammatory pulmonary diseases as well as for the aforementioned single inflammatory pulmonary diseases, respectively. Preferentially, the present application refers to the prophylaxis or treatment of a chronic inflammatory pulmonary disease having a worldwide prevalence of 1:1500 or less, wherein 5-amino-2,3-dihydro-1,4-phthalazinedione sodium salt is used.

More preferred, the present application refers to the aforementioned embodiment, wherein crystalline polymorphic Forms I, II or III of 5-amino-2,3-dihydro-1,4-phthalazinedione sodium salt as defined above by their respective d values and/or 2-theta values determined by means of x-ray powder diagrams are used.

Most preferred, the present application refers to the aforementioned embodiments, wherein crystalline polymorphic Form I of 5-amino-2,3-dihydro-1,4-phthalazinedione sodium salt as defined above by their respective d values and/or 2-theta values determined by means of x-ray powder diagrams is used.

5-amino-2,3-dihydro-1,4-phthalazinedione or one of its pharmaceutically acceptable salts, a composition according to the invention or a drug combination according to the invention can be applied in the prophylaxis or treatment of a chronic inflammatory pulmonary disease having a worldwide prevalence of 1:1500 or less by any medically acceptable administration route to a patient in need thereof. Such medically acceptable administration routes can be e.g. by inhalation, by intubation, orally, parenterally, intraperitoneally, intravenously, intraarterially, intramuscularly, topically, transdermally, subcutaneously, intradermally, sublingually, conjunctivally, intravaginally, rectally, intrathecally, pharyngeally or nasally.

In particular, the present disclosure relates also to such an application route of 5-amino-2,3-dihydro-1,4-phthalazinedione or one of its pharmaceutically acceptable salts in the prophylaxis or treatment of a chronic inflammatory pulmonary disease having a worldwide prevalence of 1:1700 or less, or 1:2000 or less, or 1:2500 or less, or 1:3000 or less, or 1:4000 or less, or 1:5000 or less, or 1:6000 or less, or 1:7000 or less, or 1:8000 or less, or 1:9000 or less, or 1:10000 or less.

Alternatively, the disclosure refers also to such an application route of 5-amino-2,3-dihydro-1,4-phthalazinedione or one of its pharmaceutically acceptable salts in the prophylaxis or treatment of a chronic inflammatory pulmonary disease having a worldwide prevalence in the range of 1:1500 to 1:2000000, or 1:1700 to 1:2000000, or 1:2000 to 1:2000000, or 1:2500 to 1:2000000, or 1:3000 to 1:2000000, or 1:4000 to 1:2000000, or 1:5000 to 1:2000000, or 1:6000 to 1:2000000, or 1:7000 to 1:2000000, or 1:8000 to 1:2000000, or 1:9000 to 1:2000000, or 1:10000 to 1:2000000.

Preferred oral formulations for use in the prophylaxis or treatment of a chronic inflammatory pulmonary disease having a worldwide prevalence of 1:1500 or less are capsules or tablets containing 5-amino-2,3-dihydro-1,4-phthalazinedione or one of its pharmaceutically acceptable salts in an amount of 50 mg, 100 mg, 150 mg, 200 mg, 300 mg, 400 mg, 500 mg or 600 mg, preferably 100 mg, 150 mg, 200 mg, 300 mg or 400 mg, most preferably 300 mg.

In another aspect of the invention a composition for use in the prophylaxis or treatment of a chronic inflammatory pulmonary disease is disclosed, wherein said composition contains 5-amino-2,3-dihydro-1,4-phthalazinedione or one of its pharmaceutically acceptable salts, a carrier and at least one pharmaceutically acceptable excipient.

In particular, the present disclosure refers to a composition for use in the prophylaxis or treatment of a chronic inflammatory pulmonary disease having a worldwide prevalence of 1:1500 or less, wherein said composition contains 5-amino-2,3-dihydro-1,4-phthalazinedione or one of its pharmaceutically acceptable salts, a carrier and at least one pharmaceutically acceptable excipient, and said chronic inflammatory pulmonary disease is selected from a group consisting of bronchiectasis, pulmonary alveolar microlithiasis, coalworker's pneumoconiosis, asbestosis, pneumoconiosis due to talc dust, silicosis, aluminosis of lung, bauxite fibrosis of lung, berylliosis, graphite fibrosis of lung, siderosis, stannosis, pneumoconiosis associated with tuberculosis, byssinosis, flax-dresser's disease, cannabinosis, farmer's lung, bagassosis, bird fancier's lung, suberosis, maltworker's lung, mushroom-worker's lung, maple-bark-stripper's lung, air-conditioner lung, humidifier lung, cheese-washer lung, coffee-worker lung, fishmeal-worker lung, furrier lung, sequiosis, allergic alveolitis, hypersensitivity pneumonitis, respiratory conditions due to inhalation of chemicals, gases, fumes and vapors, pneumonitis due to solids and liquids, radiation pneumonitis, fibrosis of lung following radiation, chronic drug-induced interstitial lung disorders, pulmonary permeability edema, high-altitude pulmonary edema, eosinophilic asthma, Löffler's pneumonia, tropical pulmonary eosinophilia, alveolar and parietoalveolar conditions, Hamman-Rich syndrome, abscess of lung with pneumonia, pyothorax, pleural plaque, pneumothorax, chylous effusion, fibrothorax, hemothorax, hemopneumothorax, hydrothorax, chronic pulmonary insufficiency following surgery, host-versus-graft disease after lung transplantation, graft-versus-host disease after lung transplantation, chronic lung allograft dysfunction, chronic lung allograft dysfunction—bronchiolitis obliterans syndrome, lung ischemia reperfusion injury, primary graft dysfunction after lung transplantation, Mendelson's syndrome, pulmonary collapse, atelectasis, interstitial emphysema, mediastinal emphysema, compensatory emphysema, mediastinitis, disorders of diaphragm, transient tachypnoea of newborn, congenital pneumonia due to viral agent, congenital pneumonia due to *Chlamydia*, congenital pneumonia due to *Staphylococcus*, congenital pneumonia due to *Streptococcus* group B, congenital pneumonia due to *Escherichia coli*, congenital pneumonia due to *Pseudomonas*, congenital pneumonia due to *Haemophilus influenzae*, congenital pneumonia due to *Klebsiella pneumoniae*, congenital pneumonia due to *Mycoplasma*, neonatal aspiration of meconium, interstitial emphysema originating in the perinatal period, pneumothorax originating in the perinatal period, pneumomediastinum originating in the perinatal period, pulmonary hemorrhage originating in the perinatal period, and Wilson-Mikity syndrome.

In particular, the disclosure refers also to such a composition comprising 5-amino-2,3-dihydro-1,4-phthalazinedione or one of its pharmaceutically acceptable salts, a carrier and at least one pharmaceutically acceptable excipient for use in the prophylaxis or treatment of a chronic inflammatory pulmonary disease having a worldwide prevalence of 1:1700 or less, or 1:2000 or less, or 1:2500 or less, or 1:3000 or less, or 1:4000 or less, or 1:5000 or less, or 1:6000 or less, or 1:7000 or less, or 1:8000 or less, or 1:9000 or less, or 1:10000 or less.

Alternatively, the disclosure refers also to a composition of 5-amino-2,3-dihydro-1,4-phthalazinedione or one of its pharmaceutically acceptable salts, a carrier and at least one pharmaceutically acceptable excipient for use in the prophylaxis or treatment of a chronic inflammatory pulmonary disease having a worldwide prevalence in the range of 1:1500 to 1:2000000, or 1:1700 to 1:2000000, or 1:2000 to 1:2000000, or 1:2500 to 1:2000000, or 1:3000 to 1:2000000, or 1:4000 to 1:2000000, or 1:5000 to 1:2000000, or 1:6000 to 1:2000000, or 1:7000 to 1:2000000, or 1:8000 to 1:2000000, or 1:9000 to 1:2000000, or 1:10000 to 1:2000000.

The term "pharmaceutically acceptable excipient(s)" refers to natural or synthetic compounds that are added to a pharmaceutical formulation alongside the pharmaceutical active agent. They may help to bulk up the formulation, to enhance the desired pharmacokinetic properties or the stability of the formulation, as well as being beneficial in the manufacturing process. Advantageous classes of excipients according to the invention include, carriers, binding agents, colorants, buffers, preservatives, antioxidants, coatings, sweeteners, thickening agents, pH-regulators, acidity regulators acidifiers, solvents, isotonizing agents, penetration enhancers, disintegrants, glidants, lubricants, emulsifiers, solubilizing agents, stabilizers, diluents, anti-caking agents (antiadherents), sorbents, foaming agents, anti-foaming agents, opacifiers, fatliquors, consistency enhancers, hydrotropes, aromatic and flavoring substances.

In general, one or more pharmaceutically acceptable carriers are added to a pharmaceutically active agent. Eligible are all carriers known in the art and combinations thereof. In solid dosage forms they can be for example plant and animal fats, waxes, paraffins, starch, tragacanth, cellulose derivatives, polyethylene glycols, silicones, bentonites, silica, talcum, zinc oxide. For liquid dosage forms and emulsions suitable carriers are for example solvents, solubilizing agents, emulsifiers such as water, ethanol, isopropanol, ethyl carbonate, ethyl acetate, benzyl alcohol, benzyl benzoate, propylene glycol, 1,3-butyl glycol, cotton seed oil, peanut oil, olive oil, castor oil, sesame oil, glycerol fatty acid esters, polyethylglycols, fatty acid esters of sorbitan. Suspensions according to the invention may use carriers known in the art such as diluents (e.g. water, ethanol or propylene glycol), ethoxylized isostearyl alcohols, polyoxyethylene and polyoxyethylene sorbitan esters, microcrystalline cellulose, bentonites, agar agar, tragacanth.

The term binding agents refers to substances that bind powders or glue them together, rendering them cohesive through granule formation. They serve as a "glue" of the formulation. Binding agents increase the cohesive strength of the provided diluent or filler.

Suitable binding agents are for example starch from wheat, corn, rice or potato, gelatin, naturally occurring sugars such as glucose, sucrose or beta-lactose, sweeteners from corn, natural and synthetic gums such as acacia, tragacanth or ammonium calcium alginate, sodium alginate, carboxymethyl cellulose, sodium carboxymethyl cellulose, hydroxypropyl carboxymethyl cellulose, polyethylene glycol, polyvinyl pyrrolidone, magnesium aluminum silicate, waxes and others. The percentage of the binding agent in the composition can range from 1-30% by weight, preferred 2-20% by weight, more preferred 3-10% by weight and most preferred 3-6% by weight.

Colorants are excipients that bestow a colorization to the pharmaceutical formulation. These excipients can be food colorants. They can be adsorbed on a suitable adsorption means such as clay or aluminum oxide. A further advantage of a colorant is that it may visualize spilled aqueous solution on the nebulizer and/or the mouthpiece to facilitate cleaning. The amount of the colorant may vary between 0.01 and 10% per weight of the pharmaceutical composition, preferred between 0.05 and 6% per weight, more preferred between 0.1 and 4% per weight, most preferred between 0.1 and 1% per weight.

Suitable pharmaceutical colorants are for example curcumin, riboflavin, riboflavin-5'-phosphate, tartrazine, alkannin, quinolione yellow WS, Fast Yellow AB, riboflavin-5'-sodium phosphate, yellow 2G, Sunset yellow FCF, orange GGN, cochineal, carminic acid, citrus red 2, carmoisine, amaranth, Ponceau 4R, Ponceau SX, Ponceau 6R, erythrosine, red 2G, Allura red AC, Indathrene blue RS, Patent blue V, indigo carmine, Brilliant blue FCF, chlorophylls and chlorophyllins, copper complexes of chlorophylls and chlorophyllins, Green S, Fast Green FCF, Plain caramel, Caustic sulphite caramel, ammonia caramel, sulphite ammonia caramel, Black PN, Carbon black, vegetable carbon, Brown FK, Brown HT, alpha-carotene, beta-carotene, gamma-carotene, annatto, bixin, norbixin, paprika oleoresin, capsanthin, capsorubin, lycopene, beta-apo-8'-carotenal, ethyl ester of beta-apo-8'-carotenic acid, flavoxanthin, lutein, cryptoxanthin, rubixanthin, violaxanthin, rhodoxanthin, canthaxanthin, zeaxanthin, citranaxanthin, astaxanthin, betanin, anthocyanins, saffron, calcium carbonate, titanium dioxide, iron oxides, iron hydroxides, aluminum, silver, gold, pigment rubine, tannin, orcein, ferrous gluconate, ferrous lactate.

Moreover, buffer solutions are preferred for liquid formulations, in particular for pharmaceutical liquid formulations. The terms buffer, buffer system and buffer solution, in particular of an aqueous solution, refer to the capacity of the system to resist a pH change by the addition of an acid or a base, or by dilution with a solvent. Preferred buffer systems may be selected from the group comprising formate, lactate, benzoic acid, oxalate, fumarate, aniline, acetate buffer, citrate buffer, glutamate buffer, phosphate buffer, succinate, pyridine, phthalate, histidine, MES (2-(N-morpholino) ethanesulfonic acid), maleic acid, cacodylate (dimethyl arsenate), carbonic acid, ADA (N-(2-acetamido)imino diacetic acid, PIPES (4-piperazine-bis-ethanesulfonic acid), BIS-TRIS propane (1,3-bis[tris(hydroxymethyl)methylaminol] propane), ethylene diamine, ACES (2-[(amino-2-oxoethyl) amino]ethanesulfonic acid), imidazole, MOPS (3-(N-morphino) propanesulfonic acid), diethyl malonic acid, TES (2-[tris(hydroxymethyl)methyl]aminoethanesulfonic acid), HEPES (N-2-hydroxyethylpiperazine-N'-2-ethanesulfonic acid), as well as other buffers with a $pK_a$ between 3.8 and 7.7.

Preferred are carbonic acid buffers such as acetate buffer and dicarboxylic acid buffers such as fumarate, tartrate and phthalate as well as tricarboxylic acid buffers such as citrate.

A further group of preferred buffers are inorganic buffers such as sulfate hydroxide, borate hydroxide, carbonate hydroxide, oxalate hydroxide, calcium hydroxide and phosphate buffers. Another group of preferred buffers are nitrogen-containing puffers such as imidazole, diethylene diamine and piperazine. Furthermore preferred are sulfonic acid buffers such as TES, HEPES, ACES, PIPES, [(2-hydroxy-1,1-bis-(hydroxymethyl)ethyl)amino]-1-propanesulfonic acid (TAPS), 4-(2-hydroxyethyl)piperazine-1-propanesulfonic acid (EEPS), MOPS and N,N-bis-(2-hydroxyethyl)-2-aminoethanesulfonic acid (BES). Another group of preferred buffers are glycine, glycyl-glycine, glycyl-glycyl-glycine, N,N-bis-(2-hydroxyethyl)glycine and N-[2-hydroxy-1,1-bis(hydroxymethyl)ethyl]glycine (tricine). Preferred are also amino acid buffers such as glycine, alanine, valine, leucine, isoleucine, serine, threonine, phenylalanine, tyrosine, tryptophan, lysine, arginine, histidine, aspartate, glutamate, asparagine, glutamine, cysteine, methionine, proline, 4-hydroxy proline, N,N,N-trimethyllysine, 3-methyl histidine, 5-hydroxy-lysine, o-phosphoserine, gamma-carboxyglutamate, [epsilon]-N-acetyl lysine, [omega]N-methyl arginine, citrulline, ornithine and their derivatives.

Preservatives for liquid and/or solid dosage forms can be used on demand. They may be selected from the group comprising, but not limited to, sorbic acid, potassium sorbate, sodium sorbate, calcium sorbate, methyl paraben, ethyl paraben, methyl ethyl paraben, propyl paraben, benzoic acid, sodium benzoate, potassium benzoate, calcium benzoate, heptyl p-hydroxybenzoate, sodium methyl para-hydroxybenzoate, sodium ethyl para-hydroxybenzoate, sodium propyl para-hydroxybenzoate, benzyl alcohol, benzalkonium chloride, phenylethyl alcohols, cresols, cetylpyridinium chloride, chlorobutanol, thiomersal (sodium 2-(ethylmercurithio) benzoic acid), sulfur dioxide, sodium sulfite, sodium bisulfite, sodium metabisulfite, potassium metabisulfite, potassium sulfite, calcium sulfite, calcium hydrogen sulfite, potassium hydrogen sulfite, biphenyl, orthophenyl phenol, sodium orthophenyl phenol, thiabendazole, nisin, natamycin, formic acid, sodium formate, calcium formate, hexamine, formaldehyde, dimethyl dicarbonate, potassium nitrite, sodium nitrite, sodium nitrate, potassium nitrate, acetic acid, potassium acetate, sodium acetate, sodium diacetate, calcium acetate, ammonium acetate, dehydroacetic acid, sodium dehydroacetate, lactic acid, propionic acid, sodium propionate, calcium propionate, potassium propionate, boric acid, sodium tetraborate, carbon dioxide, malic acid, fumaric acid, lysozyme, copper-(II)-sulfate, chlorine, chlorine dioxide and other suitable substances or compositions known to the person skilled in the art.

The addition of a sufficient amount of antioxidants is particularly preferable for liquid and topical dosage forms. Suitable examples for antioxidants include sodium metabisulfite, alpha-tocopherol, ascorbic acid, maleic acid, sodium ascorbate, ascorbyl palmitate, butylated hydroxyanisol, butylated hydroxytoluene, fumaric acid or propyl gallate. Preferred is the use of sodium metabisulfite, alpha-tocopherol and ascorbyl palmitate.

Tablets or pills are usually coated, i.e. the coating constitutes the outer layer. This can be a film coating, a sugar coating with saccharides and a compression coating. Pharmaceutically acceptable varnishes or waxes, HPMC (hydroxypropylmethylcellulose), MC (methylcellulose) or HPC (hydroxypropylcellulose) can be used. Such a coating may help to disguise the taste, to ease the swallowing or the identification. Often plasticizers and pigments are included in the coating. Capsules normally have a gelatinous envelope that encloses the active substance. The specific composition and thickness of this gelatinous layer determines how fast absorption takes place after ingestion of the capsule. Of special interest are sustained release formulations, as known in the art.

Suitable sweeteners can be selected from the group comprising mannitol, glycerol, acesulfame potassium, aspartame, cyclamate, isomalt, isomaltitol, saccharin and its sodium, potassium and calcium salts, sucralose, alitame, thaumatin, glycyrrhizin, neohesperidine dihydrochalcone, steviol glycosides, neotame, aspartame-acesulfame salt, maltitol, maltitol syrup, lactitol, xylitol, erythritol.

Suitable thickening agents can be selected from the group comprising, but not limited to, polyvinyl pyrrolidone, methyl cellulose, hydroxypropyl methyl cellulose, hydroxypropyl cellulose, dextrins, polydextrose, modified starch, alkaline modified starch, bleached starch, oxidized starch, enzyme-treated starch, monostarch phosphate, distarch phosphate esterified with sodium trimetaphosphate or phosphorus oxychloride, phosphate distarch phosphate, acetylated distarch phosphate, starch acetate esterified with acetic anhydride, starch acetate esterified with vinyl acetate, acetylated distarch adipate, acetylated distarch glycerol, distarch glycerin, hydroxypropyl starch, hydroxy propyl distarch glycerin, hydroxypropyl distarch phosphate, hydroxypropyl distarch glycerol, starch sodium octenyl succinate, acetylated oxidized starch, hydroxyethyl cellulose.

Suitable pH-regulators for liquid dosage forms are e.g. sodium hydroxide, hydrochloric acid, buffer substances such as sodium dihydrogen phosphate or disodium hydrogenphosphate.

Suitable acidity regulators can be selected from the group comprising acetic acid, potassium acetate, sodium acetate, sodium diacetate, calcium acetate, carbon dioxide, malic acid, fumaric acid, sodium lactate, potassium lactate, calcium lactate, ammonium lactate, magnesium lactate, citric acid, mono-, di-, trisodium citrate, mono-, di-, tripotassium citrate, mono-, di-, tricalcium citrate, tartaric acid, mono-, disodium tartrate, mono-, dipotassium tartrate, sodium potassium tartrate, ortho-phosphoric acid, lecithin citrate, magnesium citrate, ammonium malate, sodium malate, sodium hydrogen malate, calcium malate, calcium hydrogen malate, adipic acid, sodium adipate, potassium adipate, ammonium adipate, succinic acid, sodium fumarate, potassium fumarate, calcium fumarate, ammonium fumarate, 1,4-heptonolactone, triammonium citrate, ammonium ferric citrate, calcium glycerophosphate, isopropyl citrate, potassium carbonate, potassium bicarbonate, ammonium carbonate, ammonium bicarbonate, magnesium carbonate, magnesium bicarbonate, ferrous carbonate, ammonium sulfate, aluminum potassium sulfate, aluminum ammonium sulfate, sodium hydroxide, potassium hydroxide, ammonium hydroxide, magnesium hydroxide, gluconic acid.

Acidifiers use to be inorganic chemicals that either produce or become acid. Suitable examples are: Ammonium chloride, calcium chloride.

Suitable solvents may be selected from the group comprising, but not limited to, water, carbonated water, water for injection, water with isotonizing agents, saline, isotonic saline, alcohols, particularly ethyl and n-butyl alcohol, and mixtures thereof.

Suitable isotonizing agents are for example pharmaceutically acceptable salts, in particular sodium chloride and potassium chloride, sugars such as glucose or lactose, sugar alcohols such as mannitol and sorbitol, citrate, phosphate, borate and mixtures thereof.

Penetration enhancers (permeation or permeability enhancers) are substances that temporarily diminish the barrier of the skin and promote or accelerate the absorption of cosmetic agents. Suitable penetration enhancers can be selected from the group comprising, but not limited to, dimethyl isosorbide (Arlasolve®), dimethyl sulfoxide (DMSO) and its analogues, dimethyl formamide (DMF), azone (1-dodecylazacycloheptan-2-one), pyrrolidones such as 2-pyrrolidone, fatty acids such as oleic acid, lauric acid, myristic acid and capric acid, nonic surfactants such as polyoxyethylene-2-oleyl ether and polyoxyethylene-2-stearyl ether, terpenes, terpenoids and sesquiterpenes such as those from essential oils of eucalyptus, chenopodium and ylang-ylang, oxazolidinones such as 4-decyloxazolidin-2-one, turpentine oil, pine oil, menthol.

Suitable disintegrants can be selected from the group comprising starch, cold water-soluble starches such as carboxymethyl starch, cellulose derivatives such as methyl cellulose and sodium carboxymethyl cellulose, microcrystalline cellulose and cross-linked microcrystalline celluloses such as croscarmellose sodium, natural and synthetic gums such as guar, agar, karaya (Indian tragacanth), locust bean gum, tragacanth, clays such as bentonite, xanthan gum, alginates such as alginic acid and sodium alginate, foaming compositions a.o. Moisture expansion is supported by for example starch, cellulose derivatives, alginates, polysaccharides, dextrans, cross-linked polyvinyl pyrrolidone. The amount of the disintegrant in the composition may vary between 1 and 40% per weight, preferred between 3 and 20% per weight, most preferred between 5 and 10% per weight.

Glidants are materials that prevent a baking of the respective supplements and improve the flow characteristics of granulations so that the flow is smooth and constant. Suitable glidants comprise silicon dioxide, magnesium stearate, sodium stearate, starch and talcum. The amount of the glidant in the composition may vary between 0.01 and 10% per weight, preferred between 0.1 and 7% per weight, more preferred between 0.2 and 5% per weight, most preferred between 0.5 and 2% per weight.

The term lubricants refers to substances that are added to the dosage form in order to facilitate tablets, granulates etc. to be released from the press mold or the outlet nozzle. They diminish friction or abrasion. Lubricants are usually added shortly before pressing, as they should be present on the surface of the granules and between them and the parts of the press mold. The amount of the lubricant in the composition may vary between 0.05 and 15% per weight, preferred between 0.2 and 5% per weight, more-preferred between 0.3 and 3% per weight, most preferred between 0.3 and 1.5% per weight. Suitable lubricants are a.o. sodium oleate, metal stearates such as sodium stearate, calcium stearate, potassium stearate and magnesium stearate, stearic acid, sodium benzoate, sodium acetate, sodium chloride, boric acid, waxes having a high melting point, polyethylene glycol.

Emulsifiers can be selected for example from the following anionic and non-ionic emulsifiers: Anionic emulsifier waxes, cetyl alcohol, cetylstearyl alcohol, stearic acid, oleic acid, polyoxyethylene polyoxypropylene block polymers, addition products of 2 to 60 mol ethylene oxide to castor oil and/or hardened castor oil, wool wax oil (lanolin), sorbitan esters, polyoxyethylene alkyl esters, polyoxyethylene sorbitan fatty acid esters, polyoxyethene sorbitan monolaurate, polyoxyethene sorbitan monooleate, polyoxyethene sorbitan monopalmitate, polyoxyethene sorbitan monostearate, polyoxyethene sorbitan tristearate, polyoxyethene stearate, polyvinyl alcohol, metatartaric acid, calcium tartrate, alginic acid, sodium alginate, potassium alginate, ammonium alginate, calcium alginate, propane-1,2-diol alginate, carrageenan, processed eucheuma seaweed, locust bean gum, tragacanth, acacia gum, karaya gum, gellan gum, gum ghatti, glucomannane, pectin, amidated pectin, ammonium phosphatides, brominated vegetable oil, sucrose acetate isobutyrate, glycerol esters of wood rosins, disodium phosphate, trisodium diphosphate, tetrasodium diphosphate, dicalcium diphosphate, calcium dihydrogen diphosphate, sodium triphosphate, pentapotassium triphosphate, sodium polyphosphates, sodium calcium polyphosphate, calcium polyphosphates, ammonium polyphosphate, beta-cyclodextrin, powdered cellulose, methyl cellulose, ethyl cellulose, hydroxypropyl cellulose, hydroxypropyl methylcellulose, ethyl methyl cellulose, carboxymethyl cellulose, sodium carboxymethyl cellulose, ethyl hydroxyethyl cellulose, croscarmellose, enzymically hydrolyzed carboxymethyl cellulose, mono- and diglycerides of fatty acids, glyceryl monostearate, glyceryl distearate, acetic acid esters of mono- and diglycerides of fatty acids, lactic acid esters of mono- and diglycerides of fatty acids, citric acid esters of mono- and diglycerides of fatty acids, tartaric acid esters of mono- and diglycerides of fatty acids, mono- and diacetyl tartaric acid esters of mono- and diglycerides of fatty acids, mixed acetic and tartaric acid esters of mono- and diglycerides of fatty acids, succinylated monoglycerides, sucrose esters of fatty acids, sucroglycerides, polyglycerol esters of fatty acids, polyglycerol polyricinoleate, propane-1,2-diol esters of fatty acids, propylene glycol esters of fatty acids, lactylated fatty acid esters of glycerol and propane-1, thermally oxidized soy bean oil interacted with mono- and diglycerides of fatty acids, dioctyl sodium sulphosuccinate, sodium stearoyl-2-lactylate, calcium stearoyl lactylate, stearyl tartrate, stearyl citrate, sodium stearoyl fumarate, calcium stearoyl fumarate, stearyl tartrate, stearyl citrate, sodium stearoyl fumarate, calcium stearoyl fumarate, sodium laurylsulfate, ethoxylated mono- and diglycerides, methyl glucoside-coconut oil ester, sorbitan monostearate, sorbitan tristrearate, sorbitan monolaurate, sorbitan monooleate, sorbitan monopalmitate, sorbitan trioleate, calcium sodium polyphosphate, calcium polyphosphate, ammonium polyphosphate, cholic acid, choline salts, distarch glycerol, starch sodium octenyl succinate, acetylated oxidized starch. Preferred are glycerin monooleate, stearic acid, phospholipids such as lecithin.

Suitable as surface-active solubilizing agents (solubilizers) are for example diethylene glycol monoethyl ester, polyethyl propylene glycol co-polymers, cyclodextrins such as α- and β-cyclodextrin, glyceryl monostearates such as Solutol HS 15 (Macrogol-15-hydroxystearate from BASF, PEG 660-15 hydroxystearates), sorbitan esters, polyoxyethylene glycol, polyoxyethylene sorbitanic acid esters, polyoxyethylene sorbitan monooleate, polyoxyethylene oxystearic acid triglyceride, polyvinyl alcohol, sodium dodecyl sulfate, (anionic) glyceryl monooleates.

Stabilizers are substances that can be added to prevent unwanted changes. Though stabilizers are not real emulsifiers they may also contribute to the stability of emulsions. Suitable examples for stabilizers are oxystearin, xanthan gum, agar, oat gum, guar gum, tara gum, polyoxyethene stearate, aspartame-acesulfame salt, amylase, proteases, papain, bromelain, ficin, invertase, polydextrose, polyvinyl pyrrolidone, polyvinyl polypyrrolidone, triethyl citrate, maltitol, maltitol syrup.

Diluents or fillers are inactive substances added to drugs in order to handle minimal amounts of active agents. Examples for suitable diluents are water, mannitol, pregelatinized starch, starch, microcrystalline cellulose, powdered cellulose, silicified microcrystalline cellulose, dibasic calcium phosphate dihydrate, calcium phosphate, calcium carbonate, hydroxypropyl cellulose, hydroxyethyl cellulose, hydroxypropyl methylcellulose, polyethylene glycol, xanthum gum, gum arabic or any combination thereof.

Anti-caking agents (antiadherents) can be added to a supplement or a composition of supplements in order to prevent the formation of lumps and for easing packaging, transport, release from the at least one chamber of the dispensing cap and consumption. Suitable examples include tricalcium phosphate, powdered cellulose, magnesium stearate, sodium bicarbonate, sodium ferrocyanide, potassium ferrocyanide, calcium ferrocyanide, bone phosphate, sodium silicate, silicon dioxide, calcium silicate, magnesium trisilicate, talcum powder, sodium aluminosilicate, potassium aluminum silicate, calcium aluminosilicate, bentonite, aluminum silicate, stearic acid, polydimethyl siloxane.

Sorbents are materials that soak up oil from the water. Suitable examples include natural sorbents such as peat moss, sawdust, feathers, and anything else natural that contains carbon and synthetic sorbents such as, polyethylene and nylon. Sorbents are used for tablet/capsule moisture-proofing by limited fluid sorbing (taking up of a liquid or a gas either by adsorption or by adsorption) in a dry state.

In some galenic formulations it may be desirable that a liquid oral dosage form generates some foam on being dissolved. Such an effect can be supported through the addition of a foaming agent that reduces the surface tension of the liquid, thus facilitating the formation of bubbles, or it increases its colloidal stability by inhibiting coalescence of bubbles. Alternatively, it may stabilize foam. Suitable examples include mineral oil, *quillaia* extract, triethyl citrate, sodium lauryl ether sulfate, sodium lauryl sulfate, ammonium lauryl sulfate.

Alternatively, some liquid oral dosage forms may appear slightly foamy upon preparation. Though this does not interfere with the desired application it may affect patient compliance in case of a medication or the commercial success in case of dietary supplements. Therefore, it may be desirable to add a pharmaceutically acceptable anti-foaming agent (defoamer). Examples are polydimethylsiloxane or silicone oil in dietary supplements or simethicone in pharmaceuticals.

Opacifiers are substances that render the liquid dosage for, opaque, if desired. They must have a refractive index substantially different from the solvent, in most cases here water. At the same time, they should be inert to the other components of the composition. Suitable examples include titanium dioxide, talc, calcium carbonate, behenic acid, cetyl alcohol, or mixtures thereof.

Suitable fatliquors are e.g. oleic acid decylester, hydrated castor oil, light mineral oil, mineral oil, polyethylene glycol, sodium laurylsulfate.

Consistency enhancers are e.g. cetyl alcohol, cetyl ester wax, hydrated castor oil, microcrystalline waxes, non-ionic emulsifier waxes, beeswax, paraffin or stearylic alcohol.

Suitable hydrotropes are alcohols such as ethanol, isopropyl alcohol or polyols such as glycerin.

Suitable aromatic and flavoring substances comprise above all essential oils that can be used for this purpose. In general, this term refers to volatile extracts from plants or parts of plants with the respective characteristic smell. They can be extracted from plants or parts of plants by steam distillation.

Suitable examples are: Essential oils, respectively aromatic substances from sage, cloves, chamomile, anise, star anise, thyme, tea tree, peppermint, mint oil, menthol, cineol, borneol, zingerol, eucalyptus oil, mango, figs, lavender oil, chamomile blossoms, pine needles, cypress, oranges, rosewood, plum, currant, cherry, birch leaves, cinnamon, limes, grapefruit, tangerine, juniper, valerian, lemon balm, lemon grass, palmarosa, cranberry, pomegranate, rosemary, ginger, pineapple, guava, echinacea, ivy leave extract, blueberry, kaki, melons etc. or mixtures thereof, as well as mixtures of menthol, peppermint and star anise oil or menthol and cherry flavor.

These aromatic or flavoring substances can be included in the range of 0.0001 to 10% per weight (particularly in a composition), preferred 0.001 to 6% per weight, more preferred 0.001 to 4% per weight, most preferred 0.01 to 1% per weight, with regard to the total composition. Application- or single case-related it may be advantageous to use differing quantities.

According to the invention all of the aforementioned excipients and classes of excipients can be used without limitation alone or in any conceivable combination thereof, as long as the inventive use is not thwarted, toxic actions may occur, or respective national legislations are infracted.

5-amino-2,3-dihydro-1,4-phthalazinedione or one of its acceptable salts can be used as monotherapy or can further be combined with at least one further active ingredient selected from a group comprising active ingredients used in disease-modifying therapies of chronic inflammatory pulmonary diseases having a worldwide prevalence of 1:1500 or less, in symptomatic therapies of a chronic inflammatory pulmonary disease having a worldwide prevalence of 1:1500 or less and in the treatment of comorbidities.

Comorbidities can result from impairments due to a chronic inflammatory pulmonary disease having a worldwide prevalence of 1:1500 or less or are independent thereof. Thus, 5-amino-2,3-dihydro-1,4-phthalazinedione or one of its pharmaceutically acceptable salts can be combined with at least one further active agent for use in the prophylaxis or treatment of a chronic inflammatory pulmonary disease having a worldwide prevalence of 1:1500 or less, wherein said chronic inflammatory pulmonary disease is selected from a group consisting of bronchiectasis, pulmonary alveolar microlithiasis, coalworker's pneumoconiosis, asbestosis, pneumoconiosis due to talc dust, silicosis, aluminosis of lung, bauxite fibrosis of lung, berylliosis, graphite fibrosis of lung, siderosis, stannosis, pneumoconiosis associated with tuberculosis, byssinosis, flax-dresser's disease, cannabinosis, farmer's lung, bagassosis, bird fancier's lung, suberosis, maltworker's lung, mushroom-worker's lung, maple-bark-stripper's lung, air-conditioner lung, humidifier lung, cheese-washer lung, coffee-worker lung, fishmeal-worker lung, furrier lung, sequiosis, allergic alveolitis, hypersensitivity pneumonitis, respiratory conditions due to inhalation of chemicals, gases, fumes and vapors, pneumonitis due to solids and liquids, radiation pneumonitis, fibrosis of lung following radiation, chronic drug-induced interstitial lung disorders, pulmonary permeability edema, high-altitude pulmonary edema, eosinophilic asthma, Löffler's pneumonia, tropical pulmonary eosinophilia, alveolar and parietoalveolar conditions, Hamman- Rich syndrome, abscess of lung with pneumonia, pyothorax, pleural plaque, pneumothorax, chylous effusion, fibrothorax, hemothorax, hemopneumothorax, hydrothorax, chronic pulmonary insufficiency following surgery, host-versus-graft disease after lung transplantation, graft-versus-host disease after lung transplantation, chronic lung allograft dysfunction, chronic lung allograft dysfunction—bronchiolitis obliterans syndrome, lung ischemia reperfusion injury, primary graft dysfunction after lung transplantation, Mendelson's syndrome, pulmonary collapse, atelectasis, interstitial emphysema, mediastinal emphysema, compensatory emphysema, mediastinitis, disorders of diaphragm, transient tachypnoea of newborn, congenital pneumonia due to viral agent, congenital pneumonia due to *Chlamydia*, congenital pneumonia due to *Staphylococcus*, congenital pneumonia due to *Streptococcus* group B, congenital pneumonia due to *Escherichia coli*, congenital pneumonia due to *Pseudomonas*, congenital pneumonia due to *Haemophilus influenzae*, congenital pneumonia due to *Klebsiella pneumoniae*, congenital pneumonia due to *Mycoplasma*, neonatal aspiration of meconium, interstitial emphysema originating in the perinatal period, pneumothorax originating in the perinatal period, pneumomediastinum originating in the perinatal period, pulmonary hemorrhage originating in the perinatal period and Wilson-Mikity syndrome, and said at least one further active agent is selected from a group comprising steroidal and non-steroidal anti-inflammatory drugs; immunomodulators; immunostimulatory agents; immunosuppressive agents; antibiotics; antiviral agents; antifungal agents; antiprotozoal agents; analgesics; anticoagulants; antiplatelet drugs; bronchodilators; pulmonary vasodilators; mucolytic agents; pulmonary surfactants; antioxidants; ENaC-activating agents; HMG-CoA reductase inhibitors, calcium antagonists or $AT_1$ receptor antagonists.

In particular, the disclosure refers also to such a combination of 5-amino-2,3-dihydro-1,4-phthalazinedione or one of its pharmaceutically acceptable salts and at least one further active agent for use in the prophylaxis or treatment of a chronic inflammatory pulmonary disease having a worldwide prevalence of 1:1700 or less, or 1:2000 or less, or 1:2500 or less, or 1:3000 or less, or 1:4000 or less, or 1:5000 or less, or 1:6000 or less, or 1:7000 or less, or 1:8000 or less, or 1:9000 or less, or 1:10000 or less.

Alternatively, the disclosure refers also to such a combination of 5-amino-2,3-dihydro-1,4-phthalazinedione or one of its pharmaceutically acceptable salts, a carrier and at least one further active agent for use in the prophylaxis or treatment of a chronic inflammatory pulmonary disease having a worldwide prevalence in the range of 1:1500 to 1:2000000, or 1:1700 to 1:2000000, or 1:2000 to 1:2000000, or 1:2500 to 1:2000000, or 1:3000 to 1:2000000, or 1:4000 to 1:2000000, or 1:5000 to 1:2000000, or 1:6000 to 1:2000000, or 1:7000 to 1:2000000, or 1:8000 to 1:2000000, or 1:9000 to 1:2000000, or 1:10000 to 1:2000000.

Suitable examples for such steroidal anti-inflammatory drugs comprise corticosteroids, glucocorticoids, cortisone, cortisone acetate, hydrocortisone, hydrocortisone acetate, dexamethasone, betamethasone, prednisone, prednisolone, methylprednisolone, deltasone, triamcinolone, tixocortol pivalate, mometasone, amcinonide, budesonide, desonide, fluociconide, fluocinolone, halcinonide, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide, flunisolide, fluticasone furoate, fluticasone propionate, triamcinolone acetonide, beclomethasone dipropionate.

Suitable examples for such non-steroidal anti-inflammatory drugs (NSAIDs) comprise acetylsalicylic acid, salicylic acid and salicylates, acetaminophen (paracetamol), salsalate, diflunisal, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, phenylbutazone, mefenamic acid, meclofenamic acid, flufenamic acid, tolfenamic acid, celexoxib, rofecoxib, valdecoxib, parecoxib, lumiracoxib, etoricoxib, firocoxib, nimesulide, clonixin, licofelone, H-harpagide, flunixin, tiaprofenic acid.

Suitable examples for such immunomodulators amongst others comprise thalidomide, lenalidomide, pomalidomide and apremilast.

Suitable examples for such antiviral drugs comprise ancriviroc, aplaviroc, cenicriviroc, enfuvirtide, maraviroc, vicriviroc, amantadine, rimantadine, pleconaril, idoxuridine, aciclovir, brivudine, famciclovir, penciclovir, sorivudine, valaciclovir, cidofovir, ganciclovir, valganciclovir, sofosbusvir, foscarnet, ribavirine, taribavirine, filibuvir, nesbuvir, tegobuvir, fosdevirine, favipiravir, merimepodib, asunaprevir, balapiravir, boceprivir, ciluprevir, danoprevir, daclatasvir, narlaprevir, telaprevir, simeprevir, vanipevir, rupintrivir, fomivirsen, amenamevir, alisporivir, bevirimate, letermovir, laninamavir, oseltamivir, peramivir, renidesivir, zanamivir.

Suitable examples for such immunostimulatory agents comprise interferons (α-, β-, γ-, τ-interferon), interleukins, CSF (colony stimulating factor), PDGF (platelet-derived growth factor), EGF (epidermal growth factor), IGF (insulin-like growth factor), THF (tetrahydrofolic acid), levamisole, dimepranole, inosine.

Suitable examples for such immunosuppressive drugs comprise the groups of glucocorticoids such as listed above; cytostatic drugs such as alkylating agents (such as cyclophosphamide), antimetabolites such as methotrexate, azathioprine, mercaptopurine, fluorouracil, leflunomide, protein synthesis inhibitors and certain antibiotics such as dactinomycin, anthracyclines, mitomycin C, bleomycin and mithramycin, intercalating agents such as mitoxantrone; antibodies such as muromonab-CD3, rituximab, ustekinumab, alemtuzumab, natalizumab, basiliximab and daclizumab; drugs acting on immunophilins such as ciclosporin, tacrolimus and sirolimus, non-classified immunosuppressive agents such as beta-interferon and gamma-interferon, opioids, TNF binding proteins such as infliximab, etanercept, adalimumab; or curcumin, catechins, mycophenolic acid, fingolimod, myriocin and fumaric acid dimethyl esters.

Suitable examples for such cognitive enhancers comprise eugeroics such as armodafinil and modafinil; amphetamines such as dextroamphetamine and lisdexamfetamine; methamphetamine; racetams such as oxiracetam, piracetam, aniracetam, pramiracetam and phenylpiracetam; herbals such as *Bacopa monnieri, Panax ginseng* and *Ginkgo biloba*; Noopept (N-phenylacetyl-L-prolylglycine ethyl ester); xanthines such as caffeine; vitamin B6; vitamin B12; methylphenidate; and acetylcholinesterase inhibitors such as donepezil.

Suitable examples for such antidepressants and other mood modifying agents comprise tricyclic antidepressants such as desipramine, imipramine, amitriptyline and doxepine; tetracyclic antidepressants such as maprotiline and mirtazapine; selective serotonin reuptake inhibitors such as sertraline, citalopram and fluoxetine; serotonin-norepinephrine reuptake inhibitors such as venlafaxine, milnaciprane and duloxetine; serotonin modulators and stimulators such as nefazodone, trazodone and vilazodone; norepinephrine reuptake inhibitors such as atomoxetine, reboxetine and viloxazine; tetracyclic antidepressants such as maprotiline and mirtazapine; and monoamine oxidase inhibitors such as selegiline, isocarboxazid, tranylcypromine, selegiline and phenelzine.

Suitable examples for such agents to prevent loss of bone density comprise bisphosphonates such as alendronate, risedronate sodium, ibandronate and zoledronate; selective estrogen receptor modulators such as raloxifene; parathyroid hormone such as teriparatide; vitamin D and mineral supplements such as calcium citrate.

Suitable examples for such sleep modifying agents comprise benzodiazepines such as temazepam, diazepam, alprazolam and oxazepam; baclofen; tizanidine; melatonin (e.g. Circadin®); and eugeroics such as armodafinil and modafinil. Eugeroics are also suitable examples for agents to prevent sleep apnea.

Suitable examples for such agents to treat or prevent sexual dysfunction comprise phosphodiesterase type 5 inhibitors such as sildenafil, tadalafil and vardenafil; yohimbine, L-arginine; and herbals such as *Panax ginseng, Lepidium meyenii* and *Crocus sativus*.

Suitable examples for such agents to treat metabolic syndrome comprise biguanide drugs such as metformin; sulfonylurea drugs such as glimepiride; insulin sensitizers such as pioglitazone; lipid lowering agents such as statins, niacin, fenofibrate and gemfibrozil; ACE inhibitors such as captopril, lisinopril and enalapril; angiotensin II receptor blockers such as irbesartan, losartan and valsartan; omega-3 polyunsaturated fatty acid; and antiplatelet agents as outlined in detail below.

Suitable examples for such agents to treat skin lesions such as pressure scores or intertrigo comprise topical treatments e.g. greer's goo (nystatin powder, hydrocortisone powder and zinc oxide paste), triple paste (contains petrolatum, zinc oxide paste, and aluminum acetate solution) and Desitin® paste (contains zinc oxide, petrolatum, cod liver oil and Lanolin) and antibacterial creams containing e.g. silver sulfadiazine or bactroban as active agent.

Suitable examples for such antibiotics comprise imipenem, meropenem, ertapenem, cephalosporins, aztreonam, penicillins such as penicillin G and penicillin V, piperacillin, mezlocillin, ampicillin, amoxicillin, flucloxacillin, methicillin, oxacillin, clavulanic acid, sulbactam, tazobactam, sultamicillin, fosfomycin, teicoplanin, vancomycin, bacitracin, colistin, gramicidin, polymyxin B, tyrothricin, teixobactin, fosmidomycin, amikacin, gentamicin, kanamycin, neomycin, netilmicin, streptomycin, tobramycin, chloramphenicol, fusidic acid, cethromycin, narbomycin, telithromycin, clindamycin, lincomycin, daptomycin, dalfopristin, quinupristin, azithromycin, clarithromycin, erythromycin, roxithromycin, linezolid, doxycycline, minocycline, tetracycline, oxytetracycline, tigecycline, norfloxacin, enoxacin, ciprofloxacin, ofloxacin, levofloxacin, moxifloxacin, metronidazole, tinidazole, aminocumarine, sulfadiazine, sulfadoxin, sulfamethoxazole, sulfasalazine, pyrimethamine, trimethoprim, rifampicin.

Anti-infective agents is a generic term for compounds that are useful in the treatment of bacterial, viral, fungal, and parasite infections (e.g. protozoa or worms) and comprises antibiotics, antiviral agents, antimycotics agents, antiprotozoal and anthelminthic agents, as well as insecticides.

Suitable examples for such antiplatelet agents comprise abciximab, acetylsalicylic acid, dipyridamole, clopidogrel, eptifibatide, ilomedin, prostacyclin, prasugrel, ticagrelor, ticlopidine and tirofiban.

Suitable examples for such muscle relaxants comprise tercuronium, 1-ethylcarbamoyl-3-(3-trifluoromethylphenyl) pyrrolidine, metaxalone, methocarbamol, meprobamate, baclofen, carisoprodol, chlorzoxanzone, cyclobenzaprine, dantrolene, diazepam, orphenadrine, quinine, rocuronium, succinylcholine, decamethonium, pancuronium, veruronium, rapacuronium, dacuronium, duador, malouetine, dipyrandium, pipercuronium, chandonium, HS-342, atracurium, mivacurium, doxacurium, d-tubocurarine, dimethyltubocurarine, gallamine, alcuronium, anatruxonium, diadonium, fazadinium, tropeinium, cisatrucurium.

Suitable examples for such antifungal agents comprise abafungin, amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, balsam of Peru.

Suitable examples for such antiprotozoal drugs comprise metronidazole, tinidazole, ornidazole, atovaquone, clioquinol, chlorquinaldol, emetin, pentamidine isethionate, eflornithine, nitrofural, halofuginone, miltefosine, chloroquine, hydroxychloroquine, mepacrine, primaquine, amodiaquine, pamaquine, piperaquine, proguanil, cyclohunailembonate, quinine, mefloquine, pyrimethamine, artmether, artemisinine, artesunate, dihydroartemisinine, halofantrine, lumefantrine, sulfadoxine.

Suitable examples for such anthelmintics comprise mebendazole, praziquantel, albendazole, diethylcarbamazine, flubendazole, ivermectin, levamisole, metrifonate, niclosamide, oxyclozanide, oxamniquine, oxantel, piperazine, pyrantel, pyrantel pamoate, monopantel, derquantel, pelletierine sulphate, pyrvinium, thiabendazole, fenbendazole, triclabendazole, abamectin, suramine, emodepside, pyrvinium embonate, aminoacetonitrile.

Suitable examples for further antiparasitic drugs comprise meglumine antimoniate, benznidazole, sodium stibogluconate, fumagillin, halofantrine, melarsoprol, nifurtimox, nitazoxanide, permethrin, lindane, malathion, carbaryl, pyrethrum, phenothrin, bio-allethrin, imidacloprid, moxidectin, nitenpyram, fipronil, pyriprol, selamectin, dimpylate, spinosad, indoxacarb, methoprene, pyriproxyfen, lufenuron, neem oil, citronella oil, clove oil, peppermint oil, eucalyptus oil.

Suitable examples for such local anesthetics comprise lidocaine, lignocaine, menthol, articaine, bupivacaine, ropivacaine, benzocaine, chloroprocaine, cocaine, cyclomethycaine, dimetociane, larocaine, piperocaine, propoxycaine, procaine, novocaine, proparacaine, tetracaine, amethocaine, cinchocaine, dibucaine, etidocaine, levobupivacaine, meplavacaine, prilocaine, trimecaine, saxitoxin, neosaxitoxin, tetrodotoxin, eugenol.

Suitable examples for analgesics comprise the NSAIDs listed above; opioid analgesics such as morphine, fentanyl, methadone, oxycodon, carfetanyl, dihydroetorphin, ohmefentanyl, etorphin, sufentanil, remifentanil, alfentanil, buprenorphine, hydromorphone, levomethadone, hydrocodone, pintramide, nalbuphine, tapentadol, pentazocin, dihydrocodeine, codeine, pethidine, tramadol, tilidine, meptazinol, naloxone, naltrexone, diprenorphine, loperamide, apomorphine; epibatidine; scopolamine; ziconitide; cannabinoids such as tetrahydrocannabinol, cannabidiol, marinol; flupirtine; ketamine and local anesthetics listed above.

Suitable examples for such anticoagulants comprise heparins, coumarins such as phenprocoumon (marcumar) and warfarin, apixaban, rivaroxaban, edoxaban, dabigatran, ximelagatran, hirudin, lepirudin, bivalirudin, citrate, EDTA, fondaparinux, argatroban, otamixaban.

Tonic agents is a generic term that refers to substances that invigorate, tone or restore the body and its physiological functions. They may be of herbal or animal origin.

Suitable examples for such antiplatelet agents comprise abciximab, acetylsalicylic acid, dipyridamole, clopidogrel, eptifibatide, ilomedin, prostacyclin, prasugrel, ticagrelor, ticlopidine and tirofiban.

Suitable bronchodilators such as beta-2 adrenergic receptor agonists comprise short-acting beta-2 agonists (SABAs) such as salbutamol, albuterol, bitolterol, fenoterol, isoprenaline, levosalbutamol, levalbuterol, orciprenaline, pirbuterol, procaterol, ritodrine and terbutaline; long-acting beta-2 agonists (LABAs) such as arformoterol, bambuterol, clenbuterol, formoterol and salmeterol; ultra-long-acting beta-2 agonists such as abediterol, carmoterol, indacaterol, olodaterol and vilanterol, alone or combined with umeclidinium bromide and/or fluticasone furoate; beta-2 agonists with unknown time of action such as isoxsuprine, mabuterol or zilpaterol.

Suitable muscarinic anticholinergics (bronchodilating $M_3$ receptor antagonists) comprise ipratropium bromide, tiotropium bromide, oxitropium bromide, glycopyrronium bromide, aclidinium bromide, umeclidinium bromide, atropine, hyoscyamine, aclidinium bromide, 4-DAMP, darifenacin, DAU-5884, HL-031, HL-120, J-104, J-129, procyclidine, oxybutynin, tolterodine and zamifenacin.

Further bronchodilators comprise epinephrine, ephedrine, theophylline and TSG12.

A potent pulmonary vasodilator is nitric oxide. Further suitable pulmonary vasodilators are prostacyclin (prostaglandin $PGI_2$) analogues such as iloprost, epoprostenol and treprostinil.

Suitable mucolytic agents comprise N-acetylcysteine (NAC), ambroxol, bromhexine, carbocisteine, erdosteine, mecysteine and dornase alfa.

Suitable pulmonary surfactants comprise synthetic compositions such as Colfosceril palmitate, Pumactant, KL-4, Venticute and Lucinactant as well as animal-derived surfactants such as Beractant, Calfactant and Poractant alfa.

A potent antioxidant is inhaled carbon monoxide (CO).

Suitable ENaC (epithelium sodium channel) activating peptides comprise AP301 and S3969.

Suitable HMG-CoA reductase inhibitors (statins) comprise atorvastatin, alone or in combination with amlodipine and/or perindopril, cerivastatin, fluvastatin, lovastatin, alone or in combination with niacin, mevastatin, pitavastatin, pravastatin, rosuvastatin, alone or in combination with ezetimibe, simvastatin, alone or in combination with ezetimibe or niacin.

Suitable calcium antagonists comprise verapamil, gallopamil, fendiline, nimodipine, nifedipine, nitrendipine, amlodipine, felodipine, lercanidipine, nicardipine, lacidipine, isradipine, nisoldipine, nivaldipine, manidipine, clevidipine, aranidipine, azelnidipine, barnidipine, benidipine, cilnidipine, efonidipine, pranidipine, diltiazem, mibefradil, bepridil, flunarizine and fluspiriline.

Suitable $AT_1$ antagonists (angiotensin II receptor blockers; sartans) comprise losartan, valsartan, candesartan, telmisartan, irbesartan, olmesartan, eprosartan, flmasartan, azilsartan, milfasartan, pomisartan, pratosartan, ripisartan, tasosartan, saprosartan and EXP 3174.

5-amino-2,3-dihydro-1,4-phthalazinedione or one of its pharmaceutically acceptable salts and the further active ingredient can be used simultaneously, separately or sequentially in order to treat or prevent disease symptoms. The two active agents may be provided in a single dosage form or as separate formulation, each formulation containing at least one of the two active agents. One or both of the two active agents may be formulated as a bolus.

Pharmaceutical formulations suitable for oral dosage forms for 5-amino-2,3-dihydro-1,4-phthalazinedione or one of its pharmaceutically acceptable salts, a composition according to the invention or a combination according to the invention may be administered as separate units such as capsules, tablets, sugar-coated tablets or pills; powders or granulates; juices, syrups, drops, teas, solutions or suspensions in aqueous or non-aqueous liquids; edible foams or mousses; or in oil-in-water or water-in-oil in lotions.

In oral dosage forms such as a tablets or capsules the active agent can thus be combined with a non-toxic and pharmaceutically acceptable inert carrier such as ethanol, glycerin or water. Powders are produced by grinding the compound to a suitably tiny particle size and mixing them with a pharmaceutical carrier in a similar manner, e.g. an edible carbohydrate such as starch or mannitol. A flavor, preservative, dispersant or colorant can also be present.

Tablets are formulated by producing, granulating or dry-pressing a powder mixture, adding a lubricant and a disintegrants and pressing the mixture to a tablet. A powder mixture is produced by mixing a suitably ground compound with a diluent or a base as described before, and if applicable, with a binding agent such as carboxymethyl cellulose, an alginate, gelatin or polyvinyl pyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acacia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting mold. The lubricated mixture is then pressed to give tablets. The compounds according to the invention can also be combined with a free-flowing inert excipient and then pressed directly to give tablets without carrying out the granulation or dry-pressing steps.

In another aspect of the invention 5-amino-2,3-dihydro-1,4-phthalazinedione or one of its pharmaceutically acceptable salts is provided in hard gelatin capsules. They are fabricated by producing a powder mixture as described before and filling it into shaped gelatin covers. Glidants and lubricants such as highly dispersed silica, talcum, magnesium stearate, calcium stearate or polyethylene glycol can be added to the powder mixture as solids. A disintegrant or solubilizer such as agar agar, calcium carbonate or sodium carbonate can be added likewise in order to improve the availability of the medication after intake of the capsule. Additionally, suitable binding agents and/or colorants can be added to the mixture, if desirable or necessary.

In another aspect of the invention 5-amino-2,3-dihydro-1,4-phthalazinedione or one of its pharmaceutically acceptable salts is included in soft gelatin capsules (SGC). SGCs are dissolved on their passage through the gastrointestinal tract. They consist mainly of gelatin enriched with variable amounts of plasticizers such as glycerol or sorbitan. The release rate depends on the specific formulation of the SGC carrier material. They are also suitable for a sustained release of the active agent. SGCs are particularly useful for the administration of poorly water-soluble active agents.

In another aspect of the invention 5-amino-2,3-dihydro-1,4-phthalazinedione or one of its pharmaceutically acceptable salts is included in chewable tablets or hard caramels. Herein the substance is integrated into the matrix of the tablets or caramels.

Liquid dosage forms comprise solutions, suspensions and emulsions. Examples are water and water/propylene glycol solutions for parenteral injections, or the addition of a sweetener or opacifier for oral solutions, suspensions and emulsions. Liquid dosage forms may also comprise solutions for intranasal administration.

In another aspect the invention relates to 5-amino-2,3-dihydro-1,4-phthalazinedione or one of its pharmaceutically acceptable salts, a composition according to the invention or a combination according to the invention for use in the prophylaxis or treatment of a chronic inflammatory pulmonary disease having a worldwide prevalence of 1:1500 or less, wherein said substance, composition or combination is applied in the form of sublingual tablets or lozenges.

Sublingual drug delivery can be an alternative when compared to oral drug delivery as sublingually administered dosage forms bypass hepatic metabolism. A rapid onset of pharmacological effect is often desired for some drugs, especially those used in the treatment of acute disorders. Sublingual tablets disintegrate rapidly, and the small amount of saliva present is usually sufficient for achieving disintegration of the dosage form coupled with better dissolution and increased bioavailability.

The drug must be lipophilic enough to be able to partition through the lipid bilayer, but not so lipophilic such that once it is in the lipid bilayer, it will not partition out again. According to the diffusive model of absorption, the flux across the lipid bilayer is directly proportional to the concentration gradient. Therefore, lower salivary solubility results in lower absorption rates and vice versa. In general, a drug which has been formulated for sublingual should ideally have a molecular weight of less than 500 to facilitate its diffusion. The oral cavity has a narrow pH range which lies between 5.0 to 7.0. The inclusion of a suitable buffer during the formulation of an ionizable drug makes it possible to control the pH of aqueous saliva.

A lozenge (troche) is a small, disc-shaped or rhombic body composed of solidifying paste containing an astringent, antiseptic, or demulcent drug, used for local treatment of the mouth or throat, the lozenge being held in the mouth until dissolved. The vehicle or base of the loze nge is usually sugar, made adhesive by admixture with acacia or tragacanth, fruit paste, made from black or red currants, confection of rose, or balsam of tolu.

In another aspect of the invention 5-amino-2,3-dihydro-1,4-phthalazinedione or one of its pharmaceutically acceptable salts is included in a suppository. In a typical production method waxes with a low melting point as well as a mixture of fatty acid glycerides such as cocoa butter are first melted. Then the active agent is homogenously dispersed under stirring or other mixing methods. The molten homogeneous mixture is then transferred to suitable molds and cooled down until solidification.

In yet another aspect of the invention 5-amino-2,3-di-hydro-1,4-phthalazinedione or one of its pharmaceutically acceptable salts is provided as a topical application form, such as creams, emulsions, lotions, gels, hydrogels, pastes, powders, ointments, liniment, films, liposomes, dermal patches, transdermal patches, transdermal sprays or suspensions.

In yet another aspect of the invention 5-amino-2,3-di-hydro-1,4-phthalazinedione or one of its pharmaceutically acceptable salts is provided as a formulation for inhalation. For an effective prophylactic or therapeutic treatment of a chronic inflammatory pulmonary disease having a world-wide prevalence of 1:1500 or less 5-amino-2,3-dihydro-1, 4-phthalazinedione or one of its pharmaceutically accept-able salts has to reach the patient's alveoli. Therefore the particle size must be sufficiently small to reach the lowest parts of the airways of the pulmonary tissue. Metered-dose inhalers (MDI) are widely in use, e.g. in the treatment of asthma. They use to have a container, respectively canister for the pharmaceutical formulation, a metering valve, for metering the dispensed quantity and a mouthpiece for inhal-ing. The pharmaceutical dosage form consists of the drug, a liquefied gas propellant such as hydrofluoroalkanes and optionally further pharmaceutically acceptable excipients.

A specific group of MDIs are dry powder inhalers (DPI). They deliver the drug to the lungs in the form of a dry powder. Most DPIs rely on the force of patient inhalation to entrain powder from the device and subsequently break-up the powder into particles that are small enough to reach the lungs. For this reason, insufficient patient inhalation flow rates may lead to reduced dose delivery and incomplete disaggregation of the powder, leading to unsatisfactory device performance. Thus, most DPIs need a minimum inspiratory effort for proper use. Therefore, their use is limited to older children and adults.

Nebulizers use to administer the active principle in the form of a mist inhaled into the lungs. Physically, this mist is an aerosol. It is generated in the nebulizer by breaking up solutions and suspensions into small aerosol droplets that can be directly inhaled from the mouthpiece of the device. In conventional nebulizers the aerosol can be generated by mechanical force, e.g. spring force in soft mist nebulizers, or electrical force. In jet nebulizers a compressor brings oxygen or compressed air to flow at high velocity through the aqueous solution with the active principle, this way gener-ating an aerosol. A variant are pressurized metered-dose inhalers (pMDIs). Ultrasonic wave nebulizers use an elec-tronic oscillator that at high frequency causes vibration of a piezoelectric element for generating ultrasonic waves in the liquid reservoir with the active principle.

The most promising technology are vibrating mesh nebu-lizers. They normally yield a better drug delivery than jet nebulizers or ultrasonic nebulizers, but the latter two may also work in some indications. Vibrating mesh nebulizers use a mesh, respectively a polymer membrane having a very large number of laser-drilled holes. This membrane is placed between the liquid reservoir and the aerosol chamber. A piezoelectric element placed on the membrane induces high frequency vibrations of the membrane, leading to droplet formation in the aqueous solution and pressuring these droplets through the holes of the membrane into the aerosol chamber. With this technique very small droplet sizes can be generated. Moreover, a significantly shorter inhalation time for the patient can thus be achieved, a feature which dras-tically increases patient compliance. Only these vibrant mesh nebulizers are regarded to be able to generate liquid droplets with the active principle in the desired size range and bring them in a therapeutically effective amount into the patient's alveoli in a reasonable time.

Mesh nebulizers can be classified into two groups accord-ing to patient interaction: Continuous mode devices and trigger-activated devices. In continuous mode mesh nebu-lizers the nebulized aerosol is continuously released into the mouthpiece and the patient has to inhale the provided aerosol. In trigger-activated devices a defined amount of aerosol is released only upon an active and deep inspiratory breath. This way a far larger amount of active agent-containing aerosol is inhaled and reaches the lowest airways than with continuous mode devices. The latter lose a large amount of active agent-containing aerosol either to the surrounding or on the passage of the upper airways, as the aerosol release is not coupled to the respiratory cycle.

Therefore trigger-activated mesh nebulizers are preferred.

Particularly preferred are trigger-activated vibrating mesh nebulizers.

Preferred are the mesh nebulizer models PARI eFlow®rapid, Philips Respironics I-neb, Philips InnoSpire Go, M-neb® dose mesh nebulizer inhalation MN-300/8, Hcmed Deepro HCM-86C and HCM860, OMRON MicroAir U100, Aerogen® Solo, KTMED NePlus NE-SM1, Vectura Fox, Vectura Bayer Breelib™.

The most preferred vibrating mesh nebulizer models are high-end models such as PARI eFlow®rapid, PARI Velox, Philips Respironics I-neb, M-neb® dose+ mesh nebulizer inhalation MN-300/8, Aerogen® Solo, Vectura Fox, Vectura Bayer Breelib™.

Thus the present application refers to 5-amino-2,3-di-hydro-1,4-phthalazinedione or one of its pharmaceutically acceptable salts, a composition according to the invention or a combination according to the invention for use in the prophylaxis or treatment of a chronic inflammatory pulmo-nary disease having a worldwide prevalence of 1:1500 or less, wherein said substance, composition or combination is applied by inhalation by using a vibrant mesh nebulizer, metered dose-inhaler, jet nebulizer, ultrasonic nebulizer or dry-powder inhaler. In yet another aspect of the invention 5-amino-2,3-dihydro-1,4-phthalazinedione or one of its pharmaceutically acceptable salts, a composition according to the invention or a combination according to the invention for use in the prophylaxis or treatment of a chronic inflam-matory pulmonary disease having a worldwide prevalence of 1:1500 or less, wherein said substance, composition or combination is provided as an additive to the ventilation air of a cardiopulmonary bypass device. During and after tho-racic surgeries patients often need to be ventilated in such a device for an indefinite period of time until their own respiration would allow for a sufficient oxygen supply. In these cases 5-amino-2,3-dihydro-1,4-phthalazinedione or one of its pharmaceutically acceptable salts can be added to the intubated ventilation air in solid form (dry powder) or in liquid form (in an aqueous solution or as a nebulized aerosol, as described before).

In yet another aspect of the invention 5-amino-2,3-di-hydro-1,4-phthalazinedione or one of its pharmaceutically acceptable salts, a composition according to the invention or a combination according to the invention for use in the prophylaxis or treatment of a chronic inflammatory pulmo-nary disease having a worldwide prevalence of 1:1500 or less, wherein said substance, composition or combination is formulated as a retard drug.

In yet another aspect of the invention 5-amino-2,3-dihydro-1,4-phthalazinedione or one of its pharmaceutically acceptable salts, a composition according to the invention or a combination according to the invention for use in the prophylaxis or treatment of a chronic inflammatory pulmonary disease having a worldwide prevalence of 1:1500 or less, wherein said substance, composition or combination is formulated as a lyophilizate.

In yet another aspect of the invention 5-amino-2,3-dihydro-1,4-phthalazinedione or one of its pharmaceutically acceptable salts, a composition according to the invention or a combination according to the invention for use in the prophylaxis or treatment of a chronic inflammatory pulmonary disease having a worldwide prevalence of 1:1500 or less, wherein said substance, composition or combination is applied in form of liposomes, micelles, multilamellar vesicles or a cyclodextrin complex.

Moreover, a method of treatment of a chronic inflammatory pulmonary disease having a worldwide prevalence of 1:1500 or less is disclosed, wherein a therapeutically effective amount of 5-amino-2,3-dihydro-1,4-phthalazinedione or one of its pharmaceutically acceptable salts, a composition according to the invention or a combination according to the invention is administered to a patient in need thereof, and said chronic inflammatory pulmonary disease is selected from a group consisting of bronchiectasis, pulmonary alveolar microlithiasis, coalworker's pneumoconiosis, asbestosis, pneumoconiosis due to talc dust, silicosis, aluminosis of lung, bauxite fibrosis of lung, berylliosis, graphite fibrosis of lung, siderosis, stannosis, pneumoconiosis associated with tuberculosis, byssinosis, flax-dresser's disease, cannabinosis, farmer's lung, bagassosis, bird fancier's lung, suberosis, maltworker's lung, mushroom-worker's lung, maple-bark-stripper's lung, air-conditioner lung, humidifier lung, cheese-washer lung, coffee-worker lung, fishmeal-worker lung, furrier lung, sequiosis, allergic alveolitis, hypersensitivity pneumonitis, respiratory conditions due to inhalation of chemicals, gases, fumes and vapors, pneumonitis due to solids and liquids, radiation pneumonitis, fibrosis of lung following radiation, chronic drug-induced interstitial lung disorders, pulmonary permeability edema, high-altitude pulmonary edema, eosinophilic asthma, Löffler's pneumonia, tropical pulmonary eosinophilia, alveolar and parietoalveolar conditions, Hamman-Rich syndrome, abscess of lung with pneumonia, pyothorax, pleural plaque, pneumothorax, chylous effusion, fibrothorax, hemothorax, hemopneumothorax, hydrothorax, chronic pulmonary insufficiency following surgery, host-versus-graft disease after lung transplantation, graft-versus-host disease after lung transplantation, chronic lung allograft dysfunction, chronic lung allograft dysfunction—bronchiolitis obliterans syndrome, lung ischemia reperfusion injury, primary graft dysfunction after lung transplantation, Mendelson's syndrome, pulmonary collapse, atelectasis, interstitial emphysema, mediastinal emphysema, compensatory emphysema, mediastinitis, disorders of diaphragm, transient tachypnoea of newborn, congenital pneumonia due to viral agent, congenital pneumonia due to *Chlamydia*, congenital pneumonia due to *Staphylococcus*, congenital pneumonia due to *Streptococcus* group B, congenital pneumonia due to *Escherichia coli*, congenital pneumonia due to *Pseudomonas*, congenital pneumonia due to *Haemophilus influenzae*, congenital pneumonia due to *Klebsiella pneumoniae*, congenital pneumonia due to *Mycoplasma*, neonatal aspiration of meconium, interstitial emphysema originating in the perinatal period, pneumothorax originating in the perinatal period, pneumomediastinum originating in the perinatal period, pulmonary hemorrhage originating in the perinatal period, and Wilson-Mikity syndrome.

In particular, the present disclosure refers also to such a method of treatment of a chronic inflammatory pulmonary disease having a worldwide prevalence of 1:1700 or less, or 1:2000 or less, or 1:2500 or less, or 1:3000 or less, or 1:4000 or less, or 1:5000 or less, or 1:6000 or less, or 1:7000 or less, or 1:8000 or less, or 1:9000 or less, or 1:10000 or less.

Alternatively, the disclosure refers also to such a method of treatment of a chronic inflammatory pulmonary disease having a worldwide prevalence in the range of 1:1500 to 1:2000000, or 1:1700 to 1:2000000, or 1:2000 to 1:2000000, or 1:2500 to 1:2000000, or 1:3000 to 1:2000000, or 1:4000 to 1:2000000, or 1:5000 to 1:2000000, or 1:6000 to 1:2000000, or 1:7000 to 1:2000000, or 1:8000 to 1:2000000, or 1:9000 to 1:2000000, or 1:10000 to 1:2000000.

EXAMPLES

Example 1

5-amino-2,3-dihydro-1,4-phthalazinedione sodium salt Form I was tested in an isolated, ventilated and perfused mouse lung system that was stimulated with cigarette smoke.

The isolated, ventilated and perfused mouse lung system (ILU) is an established model for studying acute effects of various conditions and drugs on lung parenchyma and vasculature. It is mainly used for examining effects of hypoxia and for evaluating the efficacy of potential drugs on the hypoxic pulmonary vasoreaction (cf. Weissmann et al. (2006) *Proc Natl Acad Sci USA* 103: 19093-19098). Results from this experimental set-up are regarded as not only indicative for the treatment of COPD but to all inflammatory disorders of the lower airways.

C57BL/6J mice (n=25, 5 per group; male/female, 3-6 months, 20-30 g; Charles River GmbH, Sulzfeld, Germany) were anesthetized with a ketamine (100 mg/kg body weight) and xylazine (20 mg/kg body weight) intraperitoneal injection (Ceva Tiergesundheit GmbH, Dusseldorf, Germany) containing heparin (50 I.E. heparin/g body weight; Ratiopharm GmbH, Ulm, Germany). The lungs and the heart were removed from the chest cavity and placed on the ILU system (see FIGS. 1A and 1B). Lungs were ventilated in an isolated chamber using normoxic gas (21% $O_2$, 5% $CO_2$, 74% $N_2$; 150 breaths per minute at the PEEP (positive end-expiratory pressure) of 3 cm $H_2O$) and perfused with a modified Krebs-Henseleit buffer (120.0 mM NaCl, 4.3 mM KCl, 1.1 mM $KH_2PO_4$, 2.4 mM $CaCl_2$, 1.3 mM $MgCl_2$, 13.14 mM glucose, 0.25 mM hydroxyethyl starch 200000/0.5, 25.0 mM $NaHCO_3$ adjusted to a constant pH range of 7.37-7.40, 800 mM L-arginine; Serag-Wissner GmbH & Co. KG, Naila, Germany) at a temperature of 37° C. Lung weight, right and left ventricle pressure, as well as ventilatory pressure were monitored and recorded during the whole experimental procedure. After 5-10 minutes, when the lung was properly flushed and all the parameters were stable, 5-amino-2,3-dihydro-1,4-phthalazinedione sodium salt was applied by adding 150 μl of a stock solution to 15 ml of the circulating perfusion buffer. The substance was applied 10 minutes prior to the first cigarette smoke application. Cigarette smoke was applied via trachea while lung is perfused with the buffer containing 5-amino-2,3-dihydro-1,4-phthalazinedione sodium salt. Cigarette smoke was prepared freshly before each application, by burning one cigarette (research cigarettes 3R4F, University of Kentucky, USA) in one minute using normoxic gas at the flow of 1 l/min and collected in a 1 l glass bottle containing 5 g silica gel for removing the moist from the cigarette smoke. 50 ml of the cigarette smoke were taken via a syringe and applied to the lung via trachea (FIG. 1A) in deep breaths (periodic inflation for 3-4 s) over a period of 5 min. The application was done manually while carefully monitoring the inspiratory pressure to avoid damage of the lung. The cigarette smoke application was repeated three times with a 1 hour break in-between.

Five treatment groups (n=5, respectively) were investigated:

A: room air exposure

B: cigarette smoke+diluent (buffer solution)

C: cigarette smoke+0.5 mM 5-amino-2,3-dihydro-1,4-phthalazinedione sodium salt

D: cigarette smoke+1 mM 5-amino-2,3-dihydro-1,4-phthalazinedione sodium salt

E: cigarette smoke+2 mM 5-amino-2,3-dihydro-1,4-phthalazinedione sodium salt 5-amino-2,3-dihydro-1,4-phthalazinedione sodium salt Form I was dissolved in water for injection (vehicle) at the required concentrations described above. Stock solutions were prepared in water for injection. Further 1:100 dilutions were made with modified Krebs-Henseleit buffer (see above). Stock solutions were stored at −70° C. in appropriate aliquots. The required amount of stock solution was thawed, and the corresponding working solution was prepared for immediate use.

One hour after the third cigarette smoke application lungs were removed from the system and fixed by inflating with formalin solution (via trachea) at the pressure of 12-15 cm $H_2O$ for two hours at room temperature. Afterwards the fixed lungs were kept in PBS (phosphate buffer saline, see below) at +4° C. until further dehydration and paraffin embedding. Paraffin blocks were cut 3 μm thick, dried overnight at 37° C. and stained for 3-nitrotyrosine (3-NT).

The toxins and xenobiotics in the cigarette smoke lead to a dramatic increase in reactive oxygen species (ROS) and reactive nitrogen species (RNS). Oxidative and nitrosative stress correlate with the severity of inflammatory pulmonary diseases. They elevate the inflammatory response, cause a disbalance of proteolytic and anti-proteolytic activities, augment the number of apoptotic cells and decrease proliferation. These oxidants are able to overwhelm the antioxidant defenses and initiate inflammation by various mechanisms (Foronjy and D'Armiento (2006) *Clinical and Applied Immunology Reviews* 6: 53-72). The most potent RNS peroxynitrite ($ONOO^-$) is formed by reaction between nitric oxide (NO) and superoxide anion radical ($O_2^-$) (Szabo et al. (2007) *Nat Rev Drug Discov* 6: 662-680). $ONOO^-$ preferably attacks tyrosine residues in proteins to form the stable adduct 3-nitrotyrosine (Ricciardolo et al. (2004) *Physiol Rev* 84: 731-765; Seimetz et al. (2011) *Cell* 147: 293-305; Tsoumakidou et al. (2005) *Chest* 127: 1911-1918). Levels of 3-NT in sputum proteins have been found to negatively correlate with FEV1 in COPD patients (Ricciardolo et al. (2004) *Physiol Rev* 84: 731-765; Tsoumakidou et al. (2005) *Chest* 127: 1911-1918). Nitrated tyrosine residues alter cellular signalling, suggesting that 3-NT is not only a marker of nitrosative stress but may also have a functional relationship with the pathophysiology of inflammatory airway diseases (Davis et al. (2002); *J Virol* 76: 8347-8359; Murata and Kawanishi (2004) *Biochem Biophys Res Comm* 316: 123-128; Sugiura et al. (2004) *Free Radic Res* 38: 49-57;). It has been proposed that 3-NT contributes to airway hyperresponsiveness and epithelial damage (Tsoumakidou et al.

(2005) *Chest* 127: 1911-1918) and plays a major role in the development of airway remodeling (Ichinose et al. (2000) *Am J Respir Crit Care Med* 162: 701-706).

The immunohistochemical staining of 3-nitrotyrosine was carried out according to the following protocol:

| incubation time | reagent/condition | process |
|---|---|---|
| 60 min | 59° C. | deparaffinisation |
| 3 × 10 min | xylol | |
| 2 × 5 min | ethanol 99.6% | |
| 5 min | ethanol 96% | rehydratation |
| 5 min | ethanol 70% | |
| 20 min | 6% hydrogen peroxide in methanol | |
| 4 × 3 min | aqua dest | |
| 45 min | cooking in Rodent decloaker buffer (10×) | antigen retrieval |
| 30 min | cooling down | |
| wash | aqua dest | |
| 2 × 5 min | PBS pH 7.4 | |
| 60 min | 10% BSA + 1:1000 DR Fc block | |
| 4 × 5 min | PBS pH 7.4 | blocking |
| 30 min | rodent M | |
| 2 × 5 min | PBS pH 7.4 | |
| overnight + 4° C. | primary antibody (nTyr Sigma) 1:200 DR | |
| 4 × 5 min | TBS pH 7.2 | staining |
| 20 min | post block AP | |
| 2 × 5 min | TBS pH 7.2 | |
| 30 min | polymer AP kit (rabbit/mouse) | |
| 3 × 5 min | TBS pH 7.2 | |
| 1 min | aqua dest | |
| 5-10 min | Warp Red | |
| wash | TBS pH 7.2 | |
| 2 min | hematoxylin 1:10 DR | |
| wash | aqua dest | |
| 1 min | PBS pH 7.4 | |
| 5 min | DAPI in PBS 1:1000 | |
| 2 × 2 min | PBS pH 7.4 | |
| — | Dako Fluorescent Mounting Medium | covering |

Xylol was purchased from Carl Roth GmbH+Co.KG, Karlsruhe, Germany. Ethanol (96% and 99.6%) was purchased from Otto Fischar GmbH % Co.KG, Saarbrucken, Germany. Ethanol (70%) was purchased from SAV Liquid Production GmbH, Flintsbach am Inn, Germany. Hydrogen peroxide was purchased from Merck KGaA, Darmstadt, Germany. Methanol, Bovine Serum Albumin (BSA), DAPI (4',6-diamidino-2-phenylidone) and Anti-Nitrotyrosine Antibody (N0409; batch: 120M4825) were purchased from Sigma-Aldrich Co., Darmstadt, Germany. Rodent decloaker buffer (10×) and Warp Red Chromogen Kit were purchased from Biocare Medical, Pacheco, Ca., USA. Tris wash buffer (TBS), CAT hematoxylin staining solution and AP Polymer System (mouse/rabbit) were purchased from Zytomed Systems GmbH, Berlin, Germany. Dako Fluorescent Mounting Medium was purchased from Dako North America Inc., Via Real Carpinteria, Ca., USA. TruStain fcX (anti-mouse CD16/32; DR Fc block) was purchased from BioLegend Inc., San Diego, Ca., USA. PBS (phosphate-buffered saline) was prepared with 8 g/l sodium chloride (Carl Roth GmbH+Co.KG, Karlsruhe, Germany), 0.2 g/l potassium chloride (Carl Roth GmbH+Co.KG, Karlsruhe, Germany), 1.42 g/l disodium hydrogenphosphate (Merck KGaA, Darmstadt, Germany) and 0.27 g/l potassium dihydrogenphosphate (Merck KGaA, Darmstadt, Germany).

Stained histological samples were blindly analysed by light microscope. 3-nitrotyrosine levels in the lung parenchyma were quantified as a percentage of stained surface area. Quantification was performed under 200× magnification in 5-10 randomly selected fields with exclusion of large bronchi and vessels. One-Way ANOVA statistical test with Bonferroni correction was performed for comparison between groups. Differences with p<0.05 were considered statistically significant.

Cigarette smoke applied via trachea lead to a significant increase in 3-nitrotyrosine in septa of the exposed lungs (FIG. 2B), in comparison to room air as control (FIG. 2A). 5-amino-2,3-dihydro-1,4-phthalazinedione sodium salt was added to the perfusing buffer prior to the cigarette smoke application and was kept during the whole experiment. Cigarette smoke induced 3-nitrotyrosine formation could be almost completely abolished in the lungs perfused with buffer containing 1 mM 5-amino-2,3-dihydro-1,4-phthalazinedione sodium salt (FIG. 2D) or 2 mM 5-amino-2,3-dihydro-1,4-phthalazinedione sodium salt (FIG. 2E), whereas the lowest 5-amino-2,3-dihydro-1,4-phthalazinedione sodium salt concentration (0.5 mM; FIG. 2C) yielded a moderate effect.

Quantification of the Staining:

| group | mean ± SEM [% area] |
|---|---|
| A: room air | 0.24 ± 0.09 |
| B: cigarette smoke | 3.07 ± 0.39 |
| C: cigarette smoke + 0.5 mM 5-amino-2,3-dihydro-1,4-phthalazinedione sodium salt | 2.24 ± 0.28 |
| D: cigarette smoke + 1 mM 5-amino-2,3-dihydro-1,4-phthalazinedione sodium salt | 0.72 ± 0.26 |
| E: cigarette smoke + 2 mM 5-amino-2,3-dihydro-1,4-phthalazinedione sodium salt | 0.37 ± 0.13 |

Figure 3:
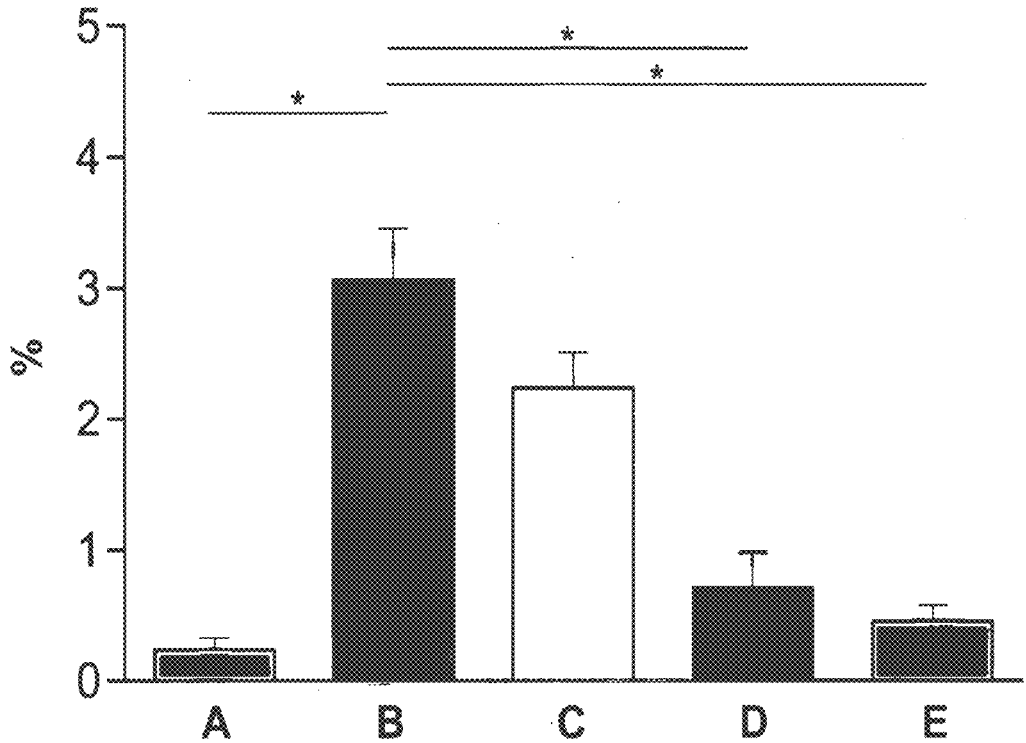

The results are depicted as bar diagrams in FIG. 3. The values (mean±SEM) indicate the percentage of the stained surface in the evaluated histological samples (5 mice per group; 5-6 evaluated histological samples per mouse).

From this experiment it can be concluded that pretreatment with 5-amino-2,3-dihydro-1,4-phthalazinedione sodium salt prevents cigarette smoke-induced 3-nitrotyrosine formation in the lung parenchyma in the ILU model.

This suggests that 5-amino-2,3-dihydro-1,4-phthalazinedione sodium salt has a protective effect against acute cigarette smoke-induced lung injury. Thus, these results can be regarded as predictive for a beneficial effect of 5-amino-2,3-dihydro-1,4-phthalazinedione and its pharmaceutically acceptable salts in the inhalatory prophylaxis or treatment of all inflammatory pulmonary diseases, in particular chronic inflammatory pulmonary diseases.

Surprisingly, the demonstrated beneficial effect of 5-amino-2,3-dihydro-1,4-phthalazinedione sodium salt against acute cigarette smoke-induced lung injury turned out to be much stronger than what could have been expected from experimental data known in the art in respect of antioxidative actions and a reduction in cytokine release.

FIGURES

FIG. 1: A: Schematic drawing of the experimental setup of Example 1

1—cigarette smoke
2—ventilator
3—trachea
4—lung
5—heart
6—reservoir

Figure 2:
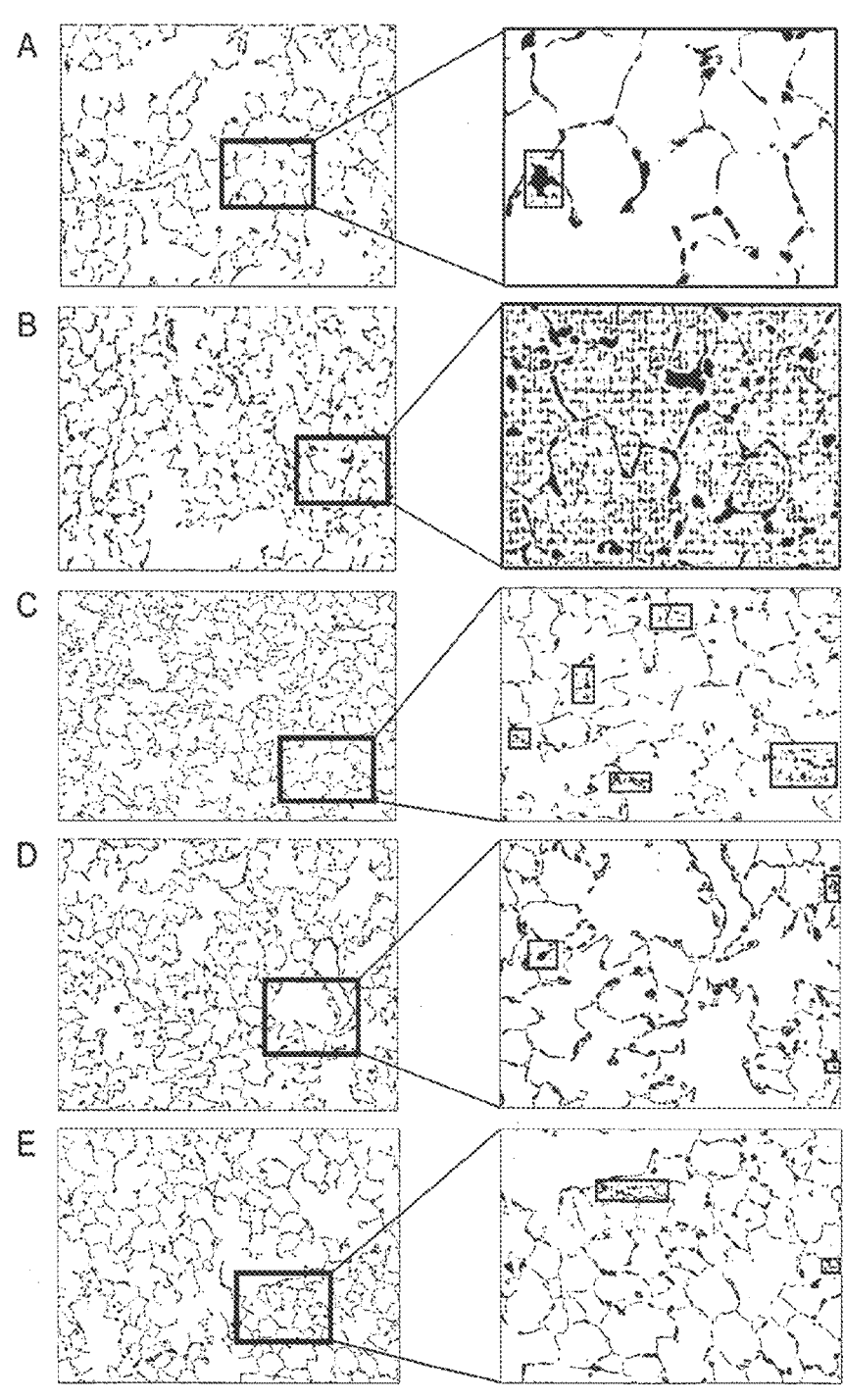

7—aqueous solution of 5-amino-2,3-dihydro-1,4-phthalazinedione sodium salt
8—roller pump FIG. 2: Immunohistochemical staining of representative samples from Example 1

Left panel: 200× magnification
Right panel: 400× magnification, enlarged detail from the left panel
A: room air
B: cigarette smoke+diluent (buffer solution)
C: cigarette smoke+0.5 mM 5-amino-2,3-dihydro-1,4-phthalazinedione sodium salt
D: cigarette smoke+1 mM 5-amino-2,3-dihydro-1,4-phthalazinedione sodium salt
E: cigarette smoke+2 mM 5-amino-2,3-dihydro-1,4-phthalazinedione sodium salt
In the right panel the inflamed areas are highlighted.

FIG. 3: Statistical evaluation of the immunohistochemical staining of samples from Example 1. The percentage of stained surface area corresponds to the grade of inflammation (n=5; mean±SEM). Bars marked with an asterisk indicate a highly significant difference between two groups (p<0.001).

A: room air
B: cigarette smoke+diluent (buffer solution)
C: cigarette smoke+0.5 mM 5-amino-2,3-dihydro-1,4-phthalazinedione sodium salt
D: cigarette smoke+1 mM 5-amino-2,3-dihydro-1,4-phthalazinedione sodium salt
E: cigarette smoke+2 mM 5-amino-2,3-dihydro-1,4-phthalazinedione sodium salt

LIST OF ABBREVIATIONS

| | |
|---|---|
| ACES | 2-[(amino-2-oxoethyl)amino]ethanesulfonic acid |
| API | active pharmaceutical ingredient |
| ARDS | adult respiratory distress syndrome |
| BES | N,N-bis-(2-hydroxyethyl)-2-aminoethanesulfonic acid |
| BOS | bronchiolitis obliterans syndrome |
| BSA | bovine serum albumin |
| CBD | chronic beryllium disease |
| CFTR | cystic fibrosis transmembrane conductance regulator |
| CLAD | chronic lung allograft dysfunction |
| CLAD-BOS | chronic lung allograft dysfunction - bronchiolitis obliterans syndrome |
| COPD | chronic obstructive pulmonary disease |
| COX | cyclooxygenase |
| CSF | colony stimulating factor |
| DAPI | 4',6-diamidino-2-phenylidone |
| DNA | deoxyribonucleic acid |
| DPI | dry powder inhaler |
| ECMO | extracorporeal membrane oxygenation |
| EDTA | ethylenediaminetetraacetic acid |
| EEPS | 4-(2-hydroxyethyl)piperazine-1-propanesulfonic acid |
| EGF | epidermal growth factor |
| ENaC | epithelial sodium channel |
| FEV1 | forced expiratory volume in the first second of expiration |
| FVC | forced vital capacity |
| HAPE | high-altitude pulmonary edema |
| HEPES | N-2-hydroxyethylpiperazine-N'-2-ethanesulfonic acid |
| ICD-10 | International Statistical Classification of Diseases and Related Health Problems, 10th revision |
| IGF | insulin-like growth factor |
| IL | interleukin |
| IR | Ischemia-reperfusion |
| LABA | long-acting beta-2 agonist |
| 5-LOX | 5-lipoxygenase |
| m² | square meter |
| MDI | metered-dose inhaler |

-continued

| MES | 2-(N-morpholino) ethanesulfonic acid |
|---|---|
| MOPS | 3-(N-morphino) propanesulfonic acid |
| μm | micrometer |
| NETS | neutrophil extracellular traps |
| NO | nitric oxide |
| NOX | NADPH oxidase |
| 3-NT | 3-nitrotyrosine |
| PBS | phosphate buffer saline |
| PDE | phosphodiesterase |
| PDGF | platelet-derived growth factor |
| PEEP | positive end-expiratory pressure |
| PEG | polyethylene glycol |
| PGD | primary graft dysfunction |
| PIPES | 4-piperazine-bis-ethanesulfonic acid |
| pMDI | pressurized metered-dose inhaler |
| PS | pulmonary sarcoidosis |
| RNS | reactive nitrogen species |
| ROS | reactive oxygen species |
| SEM | standard error of mean |
| SGC | soft gelatin capsules |
| TAPS | [(2-hydroxy-1,1-bis-(hydroxymethyl)ethyl)amino]-1-propanesulfonic acid |
| TBS | Tris wash buffer |
| TES | 2-[tris(hydroxymethyl)methyl]aminoethanesulfonic acid |
| THF | tetrahydrofolic acid |
| TNF-alpha | tumor necrosis factor-alpha |

The invention claimed is:

1. A method of treating an individual having a postprocedural or related lower respiratory disease selected from a group consisting of chronic pulmonary insufficiency following surgery, host-versus-graft disease after lung transplantation, graft-versus-host disease after lung transplantation, chronic lung allograft dysfunction, chronic lung allograft dysfunction—bronchiolitis obliterans syndrome, lung ischemia reperfusion injury, primary graft dysfunction after lung transplantation, Mendelson's syndrome, pulmonary collapse, atelectasis, interstitial emphysema, mediastinal emphysema, compensatory emphysema, mediastinitis and disorders of diaphragm by administering to such individual a pharmaceutically effective amount of 5-amino-2,3-dihydro-1,4-phthalazinedione or one of its pharmaceutically acceptable salts.

2. The method of claim 1, wherein said pharmaceutically acceptable salt of 5-amino-2,3-dihydro-1,4-phthalazinedione is 5-amino-2,3-dihydro-1,4-phthalazinedione sodium salt.

3. The method of claim 2, wherein 5-amino-2,3-dihydro-1,4-phthalazinedione sodium salt is provided as one of crystalline anhydrate polymorph forms I, II or III characterized by crystallography values determined by means of x-ray powder diagrams:
   d values: 13.5; 6.9; 5.2; 4.6; 3.9; 3.5; 3.4; 3.3; 3.1; 3.0 and/or
   2-theta values: 6.5; 12.7; 16.9; 19.3; 22.8; 25.8; 26.6; 27.2; 28.7; 30.3 for form I,
   d values: 12.9; 7.9; 7.1; 6.5; 5.3; 4.0; 3.7; 3.6; 3.3; 3.2 and/or
   2-theta values: 6.8; 11.2; 12.5; 13.7; 16.7; 22.4; 24.3; 24.9; 27.2; 27.8 for form II, and
   d values: 13.131; 7.987; 7.186; 6.566; 6.512; 5.372; 3.994; 3.662; 3.406; 3.288; 3.283; 3.222; 3.215; 3.127; 2.889 and/or
   2-theta values: 6.73; 11.07; 12.31; 13.48; 13.59; 16.49; 22.24; 24.29; 26.14; 27.10; 27.14; 27.67; 27.72; 28.52; 30.93 for form III.

4. The method of claim 1, wherein 5-amino-2,3-dihydro-1,4-phthalazinedione is provided in a composition containing 5-amino-2,3-dihydro-1,4-phthalazinedione or one of its pharmaceutically acceptable salts, a carrier and at least one pharmaceutically acceptable excipient.

5. The method of claim 4, wherein the at least one pharmaceutically acceptable excipient is selected from a group comprising binding agents, colorants, buffers, preservatives, antioxidants, coatings, sweeteners, thickening agents, pH-regulators, acidity regulators acidifiers, solvents, isotonizing agents, penetration enhancers, disintegrants, glidants, lubricants, emulsifiers, solubilizing agents, stabilizers, diluents, anti-caking agents, sorbents, foaming agents, anti-foaming agents, opacifiers, fatliquors, consistency enhancers, hydrotropes, aromatic and flavoring substances.

6. The method of claim 1, wherein 5-amino-2,3-dihydro-1,4-phthalazinedione is provided in a combination of 5-amino-2,3-dihydro-1,4-phthalazinedione or one of its pharmaceutically acceptable salts and at least one further active agent selected from a group comprising steroidal and non-steroidal anti-inflammatory drugs, immunomodulators, immunostimulatory agents, immunosuppressive agents, antibiotics, antiviral agents, antifungal agents, antiprotozoal agents, analgesics, anticoagulants, antiplatelet drugs, bronchodilators, pulmonary vasodilators, mucolytic agents, pulmonary surfactants, antioxidants, ENaC-activating agents, HMG-CoA reductase inhibitors, calcium antagonists or $AT_1$ receptor antagonists.

7. The method of claim 1, wherein 5-amino-2,3-dihydro-1,4-phthalazinedione or one of its pharmaceutically acceptable salts is applied by inhalation, by intubation, orally, parenterally, intraperitoneally, intravenously, intraarterially, intramuscularly, topically, transdermally, subcutaneously, intradermally, sublingually, conjunctivally, intravaginally, rectally, intrathecally, pharyngeally or nasally.

8. The method of claim 4, wherein said composition is applied by inhalation, by intubation, orally, parenterally, intraperitoneally, intravenously, intraarterially, intramuscularly, topically, transdermally, subcutaneously, intradermally, sublingually, conjunctivally, intravaginally, rectally, intrathecally, pharyngeally or nasally.

9. The method of claim 1, wherein 5-amino-2,3-dihydro-1,4-phthalazinedione or one of its pharmaceutically acceptable salts is applied orally in the form of tablets, soft gelatin capsules, hard gelatin capsules, sugar-coated tablets, pills, powders, granulates, juices, syrups, drops, teas, solutions or suspensions in aqueous or non-aqueous liquids, edible foams, mousses, oil-in-water lotions or water-in-oil lotions.

10. The method of claim 4, wherein said composition is applied orally in the form of tablets, soft gelatin capsules, hard gelatin capsules, sugar-coated tablets, pills, powders, granulates, juices, syrups, drops, teas, solutions or suspensions in aqueous or non-aqueous liquids, edible foams, mousses, oil-in-water lotions or water-in-oil lotions.

11. The method of claim 1, wherein 5-amino-2,3-dihydro-1,4-phthalazinedione or one of its pharmaceutically acceptable salts is applied in the form of sublingual tablets or lozenges.

12. The method of claim 4, wherein said composition is applied in the form of sublingual tablets or lozenges.

13. The method of claim 1, wherein 5-amino-2,3-dihydro-1,4-phthalazinedione or one of its pharmaceutically acceptable salts is applied by inhalation by using a vibrant mesh nebulizer, metered dose-inhaler, jet nebulizer, ultrasonic nebulizer or dry-powder inhaler.

14. The method of claim 4, wherein said composition is applied by inhalation by using a vibrant mesh nebulizer, metered dose-inhaler, jet nebulizer, ultrasonic nebulizer or dry-powder inhaler.

15. The method of claim 1, wherein 5-amino-2,3-dihydro-1,4-phthalazinedione or one of its pharmaceutically acceptable salts is added to the ventilation air of a cardiopulmonary bypass device.

16. The method of claim 4, wherein said composition is added to the ventilation air of a cardiopulmonary bypass device.

17. The method of claim 1, wherein 5-amino-2,3-dihydro-1,4-phthalazinedione or one of its pharmaceutically acceptable salts is formulated as a retard drug.

18. The method of claim 4, wherein said composition is formulated as a retard drug.

19. The method of claim 1, wherein 5-amino-2,3-dihydro-1,4-phthalazinedione or one of its pharmaceutically acceptable salts is formulated as a lyophilizate.

20. The method of claim 4, wherein said composition is formulated as a lyophilizate.

21. The method of claim 1, wherein 5-amino-2,3-dihydro-1,4-phthalazinedione or one of its pharmaceutically acceptable salts is applied in form of liposomes, micelles, multilamellar vesicles or a cyclodextrin complex.

22. The method of claim 4, wherein said composition is applied in form of liposomes, micelles, multilamellar vesicles or a cyclodextrin complex.

* * * * *